(12) United States Patent
Guyon et al.

(10) Patent No.: US 7,542,947 B2
(45) Date of Patent: Jun. 2, 2009

(54) DATA MINING PLATFORM FOR BIOINFORMATICS AND OTHER KNOWLEDGE DISCOVERY

(75) Inventors: Isabelle Guyon, Berkeley, CA (US); Edward P. Reiss, San Francisco, CA (US); René Doursat, Sun Valley, NV (US); Jason Aaron Edward Weston, New York, NY (US); David D. Lewis, Chicago, IL (US)

(73) Assignee: Health Discovery Corporation, Savannah, GA (US)

( * ) Notice: Subject to any disclaimer, the term of this patent is extended or adjusted under 35 U.S.C. 154(b) by 0 days.

(21) Appl. No.: 11/928,641

(22) Filed: Oct. 30, 2007

(65) Prior Publication Data

US 2008/0097939 A1 Apr. 24, 2008

Related U.S. Application Data

(63) Continuation of application No. 10/481,068, filed as application No. PCT/US02/19202 on Jun. 17, 2002, now Pat. No. 7,444,308, said application No. 11/928,641 is a continuation-in-part of application No. 10/478,192, filed as application No. PCT/US02/16012 on May 20, 2002, now Pat. No. 7,318,051, which is a continuation-in-part of application No. 10/057,849, filed on Jan. 24, 2002, now Pat. No. 7,117,188, which is a continuation-in-part of application No. 09/633,410, filed on Aug. 7, 2000, now Pat. No. 6,882,990.

(60) Provisional application No. 60/298,842, filed on Jun. 15, 2001, provisional application No. 60/298,757, filed on Jun. 15, 2001, provisional application No. 60/298,867, filed on Jun. 15, 2001, provisional application No. 60/191,219, filed on Mar. 22, 2000, provisional application No. 60/184,596, filed on Feb. 24, 2000, provisional application No. 60/168,703, filed on Dec. 2, 1999, provisional application No. 60/161,806, filed on Oct. 27, 1999.

(51) Int. Cl.
*G06F 7/00* (2006.01)
*G06F 17/30* (2006.01)

(52) U.S. Cl. .............................................. 706/12; 707/6
(58) Field of Classification Search .................. 706/12; 707/6
See application file for complete search history.

(56) References Cited

U.S. PATENT DOCUMENTS 5,138,694 A 8/1992 Hamilton (Continued)

FOREIGN PATENT DOCUMENTS

WO WO 01/01294 A3 1/2001

OTHER PUBLICATIONS

Kemp, "Using the Functional Data Model in Integrate Distributed Biological Data Sources", *Scientific and Statistical Database Systems Proceedings, Eighth International Conference*, Jun. 1996, pp. 176-185, Stockholm, Sweden.

(Continued)

*Primary Examiner*—David R Vincent
*Assistant Examiner*—Nathan H Brown, Jr.
(74) *Attorney, Agent, or Firm*—Procopio, Cory, Hargreaves & Savitch LLP

(57) ABSTRACT

The data mining platform comprises a plurality of system modules, each formed from a plurality of components. Each module has an input data component, a data analysis engine for processing the input data, an output data component for outputting the results of the data analysis, and a web server to access and monitor the other modules within the unit and to provide communication to other units. Each module processes a different type of data, for example, a first module processes microarray (gene expression) data while a second module processes biomedical literature on the Internet for information supporting relationships between genes and diseases and gene functionality. In the preferred embodiment, the data analysis engine is a kernel-based learning machine, and in particular, one or more support vector machines (SVMs). The data analysis engine includes a pre-processing function for feature selection, for reducing the amount of data to be processed by selecting the optimum number of attributes, or "features", relevant to the information to be discovered.

22 Claims, 12 Drawing Sheets

U.S. PATENT DOCUMENTS

| | | | |
|---|---|---|---|
| 5,495,606 | A | 2/1996 | Borden et al. |
| 5,793,964 | A | 8/1998 | Rogers et al. |
| 5,835,755 | A | 11/1998 | Stellwagen, Jr. et al. |
| 5,873,083 | A | 2/1999 | Jones et al. |
| 6,112,195 | A * | 8/2000 | Burges ........................ 706/20 |
| 6,128,608 | A | 10/2000 | Barnhill |
| 6,128,624 | A * | 10/2000 | Papierniak et al. ....... 707/104.1 |
| 6,157,921 | A | 12/2000 | Barnhill |
| 6,266,668 | B1 | 7/2001 | Vanderveldt et al. |
| 6,427,141 | B1 | 7/2002 | Barnhill |
| 6,470,277 | B1 | 10/2002 | Chin et al. |
| 6,470,333 | B1 | 10/2002 | Baclawski |
| 6,606,622 | B1 | 8/2003 | Sorace et al. |
| 6,658,395 | B1 | 12/2003 | Barnhill |
| 6,714,925 | B1 | 3/2004 | Barnhill et al. |
| 6,760,715 | B1 | 7/2004 | Barnhill et al. |
| 6,789,069 | B1 | 9/2004 | Barnhill et al. |
| 6,789,091 | B2 | 9/2004 | Gogolak |
| 6,836,773 | B2 | 12/2004 | Tamayo et al. |
| 6,882,990 | B1 | 4/2005 | Barnhill et al. |
| 6,944,602 | B2 | 9/2005 | Cristianini |
| 6,996,549 | B2 | 2/2006 | Barnhill et al. |
| 7,117,188 | B2 | 10/2006 | Guyon et al. |
| 7,299,213 | B2 | 11/2007 | Cristianini |
| 7,318,051 | B2 | 1/2008 | Weston et al. |
| 2002/0049704 | A1 | 4/2002 | Vanderveldt et al. |
| 2002/0052882 | A1 | 5/2002 | Taylor |
| 2002/0095260 | A1 | 7/2002 | Huyn |
| 2002/0111742 | A1 | 8/2002 | Rocke et al. |
| 2002/0119462 | A1 | 8/2002 | Mendrick et al. |
| 2002/0120405 | A1 | 8/2002 | Edwards et al. |
| 2002/0133504 | A1 | 9/2002 | Vlahos et al. |
| 2003/0009295 | A1 | 1/2003 | Markowitz et al. |
| 2003/0100999 | A1 | 5/2003 | Markowitz |
| 2003/0171876 | A1 | 9/2003 | Markowitz et al. |
| 2006/0064415 | A1 | 3/2006 | Guyon et al. |

OTHER PUBLICATIONS

Ben-Dor et al., "Clustering Gene Expression Patterns", *Journal of Computational Biology*, vol. 6, Nos. 3/4, 1999, pp. 281-297.

Kim et al., "Retrieval of the Top N Matches with Support Vector Machines", 2000 IEEE.

Kelly, "An Algorithm for Merging Hyperellipsoidal Clusters", 1994.

Pavlidis et al., Gene Functional Classification From Heterogeneous Data, Proceedings of the 5th International Conference on Computational Biology, Apr. 2001, pp. 249-255.

Syed et al., A Study of Support Vectors on Model Independent Example Selection, Proceedings of the 5th ACM SIGKDD International Conference on Knowledge Discovery and Data Mining, Jul. 1999, pp. 272-276.

Sevon et al., TreeDt: Gene Mapping by Tree Disequilibrium Test, 2000 ACM 1-58113-000-0/00/0000.

Pfahringer et al., Preprocessing Tasks and Methods, Mar. 1999, Austrian Research Institute for AI.

Yang et al., Data-Driven Theory Refinement Algorithms for Bioinformatics, International Joint Conference on Neural Networks, Jul. 1999, pp. 4064-4068.

Walker, R.L.,Parallel Clustering System Using the Methodologies of Evolutionary Computations, Proceedings of the 2001 Congress on Evolutionary Computation, pp. 831-838.

Moore, S.K., Harmonizing Data, Setting Standards [Genomics, Information Sets], IEEE Spectrum, Jan. 2001, vol. 38, Iss 1, pp. 111-112.

PCT/US02/19202 International Search Report issued Jan. 2, 2003.

* cited by examiner

DATA MINING PLATFORM FOR BIOINFORMATICS AND OTHER KNOWLEDGE DISCOVERY

RELATED APPLICATIONS

The present application is a continuation of application Ser. No. 10/481,068, filed Jul. 18, 2005, now U.S. Pat. No. 7,444,308 which was a U.S. national stage filing of PCT Application No. PCT/US02/19202, filed Jun. 17, 2002, and which claims the priority of each of the following U.S. provisional patent applications: Ser. No. 60/298,842, Ser. No. 60/298,757, and Ser. No. 60/298,867, all filed Jun. 15, 2001, and, for U.S. national stage purposes, is a continuation-in-part of PCT application Serial No. PCT/US02/16012, which was filed in the U.S. Receiving Office on May 20, 2002, and was filed as U.S. national stage application Ser. No. 10/478,192 on Mar. 30, 2005, now U.S. Pat. No. 7,318,051 which is a continuation-in-part of U.S. patent application Ser. No. 10/057,849, filed Jan. 24, 2002, now issued as U.S. Pat. No. 7,117,188, which is a continuation-in-part of application Ser. No. 09/633,410, filed Aug. 7, 2000, now issued as U.S. Pat. No. 6,882,990, which claims priority to U.S. provisional applications No. 60/161,806, filed Oct. 27, 1999, No. 60/168,703, filed Dec. 2, 1999, No. 60/184,596, filed Feb. 24, 2000, and No. 60/191,219, filed Mar. 22, 2000.

This application is related to, but does not claim priority to, the following applications: application Ser. No. 09/578,011, filed May 24, 2000, now issued as U.S. Pat. No. 6,658,395, which is a continuation-in-part of application Ser. No. 09/568,301, filed May 9, 2000, now issued as U.S. Pat. No. 6,427,141, which is a continuation of application Ser. No. 09/303,387, filed May 1, 1999, now issued as U.S. Pat. No. 6,128,608, which claims priority to U.S. provisional application Ser. No. 60/083,961, filed May 1, 1998. This application is related to co-pending application Ser. No. 09/633,615, now abandoned, Ser. No. 09/633,616, now issued as U.S. Pat. No. 6,760,715, Ser. No. 09/633,627, now issued as U.S. Pat. No. 6,714,925, and Ser. No. 09/633,850, now issued as U.S. Pat. No. 6,789,069, all filed Aug. 7, 2000, which are also continuations-in-part of application Ser. No. 09/578,011. This application is also related to application Ser. No. 09/303,386, now abandoned, and Ser. No. 09/305,345, now issued as U.S. Pat. No. 6,157,921, both filed May 1, 1999, and to application Ser. No. 09/715,832, filed Nov. 14, 2000, now abandoned, all of which also claim priority to provisional application Ser. No. 60/083,961. Each of the above-identified applications is incorporated herein by reference.

FIELD OF THE INVENTION

The present invention relates to the use of learning machines to identify relevant patterns in datasets containing large quantities of diverse data, and more particularly to a computational platform for extraction of data from multiple, diverse sources for identification of relevant patterns in biological data.

BACKGROUND OF THE INVENTION

Currently, most innovations in diagnosis and in therapy remain within the framework of morphology (e.g. the study of tumor shapes), physiology (the study of organ function), and chemistry.

With the advent of molecular biology and molecular genetics, medicine and pharmacology have entered the information age. Information technology, which has been so widely applied to the understanding of human intelligence (artificial intelligence, neural networks), telecommunications, and the Internet, should be applicable to the study of the program of life.

Disease used to be understood as the intrusion of foreign agents (e.g., bacteria) that should be deleted, or as a chemical imbalance that should be compensated. In the genomic era, diseases are interpreted as a deficiency of the genetic program to adapt to its environment caused by missing, lost, exaggerated or corrupted genetic information. We are moving towards an age when disease and disease susceptibility will be described and remedied not only in terms of their symptoms (phenotype), but in term of their cause: external agents and genetic malfunction (genotype).

A great deal of effort of the pharmaceutical industry is presently being directed toward detecting the genetic malfunction (diagnosis) and correcting it (cure), using the tools of modern genomic and biotechnology. Correcting a genetic malfunction can occur at the DNA level using gene therapy. The replacement of destroyed tissues due to, e.g., arthrosis, heart disease, or neuro-degeneration, could be achieved be activating natural regeneration processes, following a similar mechanism as that of embryonic development.

Most genes, when activated, yield the production of one or several specific proteins. Acting on proteins are projected to be the domain of modern drug therapy. There are two complementary ways of acting on proteins: (1) the concentration of proteins soluble in serum can be modified by using them directly as drugs; (2) chemical compounds that interact selectively with given proteins can be used as drugs.

It has been estimated that between 10,000 and 15,000 human genes code for soluble proteins. If only a small percentage of these proteins have a therapeutic effect, a considerable number of new medicinal substances based on proteins remain to be found. Presently, approximately 100 proteins are used as medicines.

All of today's drugs that are known to be safe and effective are directed at approximately 500 target molecules. Most drug targets are either enzymes (22%) or receptors (52%). Enzymes are proteins responsible for activating certain chemical reactions (catalysts). Enzyme inhibitors can, for example, halt cell reproduction for purposes of fighting bacterial infection. The inhibition of enzymes is one of the most successful strategies for finding new medicines, one example of which is the use of reverse transcriptase inhibitors to fight the infectiol,4 by the retrovirus of HIV. Receptors can be defined as proteins that form stable bonds with ligands such as hormones or neurotransmitters. Receptors can serve as "docking stations" for toxic substances to selectively poison parasites or tumor cells (chemotherapy). In the pharmacological definition, receptors are stimuli or signal transceivers. Blocking a receptor such as a neurotransmitter receptor, a hormone receptor or an ion channel alters the functioning of the cell. Since the 1950's, many successful drugs which function as receptor blockers have been introduced, including psycho-pharmaceuticals, beta-blockers, calcium antagonists, diuretics, new anesthetics, and anti-inflammatory preparations.

It can be estimated that about one thousand genes are involved in common diseases. The proteins associated with these genes may not be all good drug targets, but among the dozens of proteins that participate in the regulatory pathway, one can assume that at least three to five represent good drug targets. According to this estimate, 3,000 to 5,000 proteins could become the targets of new medicines, which is an order of magnitude greater than what is known today.

With a typical drug development process costing about $300-500 million per drug, providing a better ranking of potential leads is of the utmost importance. With the recent completion of the first draft of the human genome that revealed its 30,000 genes, and with the new microarray and combinatorial chemistry technologies, the quantity and variety of genomics data are growing at a significantly more rapid pace than the informatics capacity to analyze them.

The emphasis of molecular biology is shifting from a hypothesis driven model to a data driven model. Previously, years of intense laboratory research were required to collect data and test hypotheses regarding a single system or pathway and studying the effect of one particular drug. The new data intensive paradigm relies on a combination of proprietary data and data gathered and shared worldwide on tens of thousands of simultaneous miniaturized experiments. Bioinformatics is playing a crucial role in managing and analyzing this data.

While drug development will still follow its traditional path of animal experimentation and clinical trials for the most promising leads, it is expected that the acquisition of data from arraying technology and combinatorial chemistry followed by proper data analysis will considerably accelerate drug discovery and cut down the development cost.

Additionally, completely new areas will develop such as personalized medicine. As is known, a mix of genetic and environmental factors causes diseases. Understanding the relationships between such factors promises to improve considerably disease prevention and yield to significant health care cost savings. With genomic diagnosis, it will also be possible to prescribe a well-targeted drug, adjust the dosage and monitor treatment.

Following the challenge of genome sequencing, it is generally recognized that the two most important bioinformatics challenges are microarray data analysis (with the analysis of tens of thousands of variables) and the construction of decision systems that integrate data analysis from different sources. The essence of the problem of designing good cost-effective diagnosis test or determining good drug targets is to establish a ranking among candidate genes or proteins, the most promising ones coming at the top of the list. To be truly effective, such a ranked list must incorporate knowledge from a great variety of sources, including genomic DNA information, gene expression, protein concentration, and pharmacological and toxicological data. Challenges include: analyzing data sets with few samples but very large numbers of inputs (thousands of gene expression coefficients from only 10-20 patients); using data of poor quality or incomplete data; combining heterogeneous data sets visualizing results; incorporating the assistance of human experts complying with rules and checks for safety requirements satisfying economic constraints (e.g., selecting only one or two best leads to be pursued); in the case of an aid to decision makers, providing justifications of the system's recommendations; and in the case of personalized medicine, making the information easily accessible to the public.

Thus, the need exists for a system capable of analyzing combined data from a number of sources of varying quantity, quality and origin in order to produce useful information.

SUMMARY OF THE INVENTION

In an exemplary embodiment, the data mining platform of the present invention comprises a plurality of system modules, each formed from a plurality of components. Each module comprises an input data component, a data analysis engine for processing the input data, an output data component for outputting the results of the data analysis, and a web server to access and monitor the other modules within the unit and to provide communication to other units. Each module processes a different type of data, for example, a first module processes microarray (gene expression) data while a second module processes biomedical literature on the Internet for information supporting relationships between genes and diseases and gene functionality. In the preferred embodiment, the data analysis engine is a kernel-based learning machine, and in particular, one or more support vector machines (SVMs). The data analysis engine includes a pre-processing function for feature selection, for reducing the amount of data to be processed by selecting the optimum number of attributes, or "features", relevant to the information to be discovered. In the preferred embodiment, the feature selection means is recursive feature elimination (RFE), such that the preferred embodiment of the data analysis engine uses RFE-SVM. The output the data analysis engine of one module may be input into the data analysis engine of a different module. Thus, the output data from one module is treated as input data which would be subject to feature ranking and/or selection so that the most relevant features for a given analysis are taken from different data sources. Alternatively, the outputs of two or more modules may be input into an independent data analysis engine so that the knowledge is progressively distilled. For example, analysis results of microarray data can be validated by comparison against documents retrieved in an on-line literature search, or the results of the different modules can be otherwise combined into a single result or format.

In the preferred embodiment of the data analysis engine, pre-processing can include identifying missing or erroneous data points, or outliers, and taking appropriate steps to correct the flawed data or, as appropriate, remove the observation or the entire field from the scope of the problem. Such pre-processing can be referred to as "data cleaning". Pre-processing can also include clustering of data, which provides means for feature selection by substituting the cluster center for the features within that cluster, thus reducing the quantity of features to be processed. The features remaining after pre-processing are then used to train a learning machine for purposes of pattern classification, regression, clustering and/or novelty detection.

A test data set is pre-processed in the same manner as was the training data set. Then, the trained learning machine is tested using the pre-processed test data set. A test output of the trained learning machine may be post-processing to determine if the test output is an optimal solution based on known outcome of the test data set.

In the context of a kernel-based learning machine such as a support vector machine, the present invention also provides for the selection of at least one kernel prior to training the support vector machine. The selection of a kernel may be based on prior knowledge of the specific problem being addressed or analysis of the properties of any available data to be used with the learning machine and is typically dependant on the nature of the knowledge to be discovered from the data.

Kernels are usually defined for patterns that can be represented as a vector of real numbers. For example, linear kernels, radial basis function kernels and polynomial kernels all measure the similarity of a pair of real vectors. Such kernels are appropriate when the patterns are best represented as a sequence of real numbers.

An iterative process comparing postprocessed training outputs or test outputs can be applied to make a determination as to which kernel configuration provides the optimal solution.

If the test output is not the optimal solution, the selection of the kernel may be adjusted and the support vector machine may be retrained and retested. Once it is determined that the optimal solution has been identified, a live data set may be collected and pre-processed in the same manner as was the training data set to select the features that best represent the data. The pre-processed live data set is input into the learning machine for processing. The live output of the learning machine may then be post-processed by interpreting the live output into a computationally derived alphanumeric classifier or other form suitable to further utilization of the analysis results.

The data mining platform of the present invention provides a tailored analysis for application to novel data sources. In the preferred embodiment, support vector machines are integrated at multiple levels, e.g., at each module and for processing of the combined results of two or more modules.

DETAILED DESCRIPTION OF THE PREFERRED EMBODIMENTS

Figure 1:
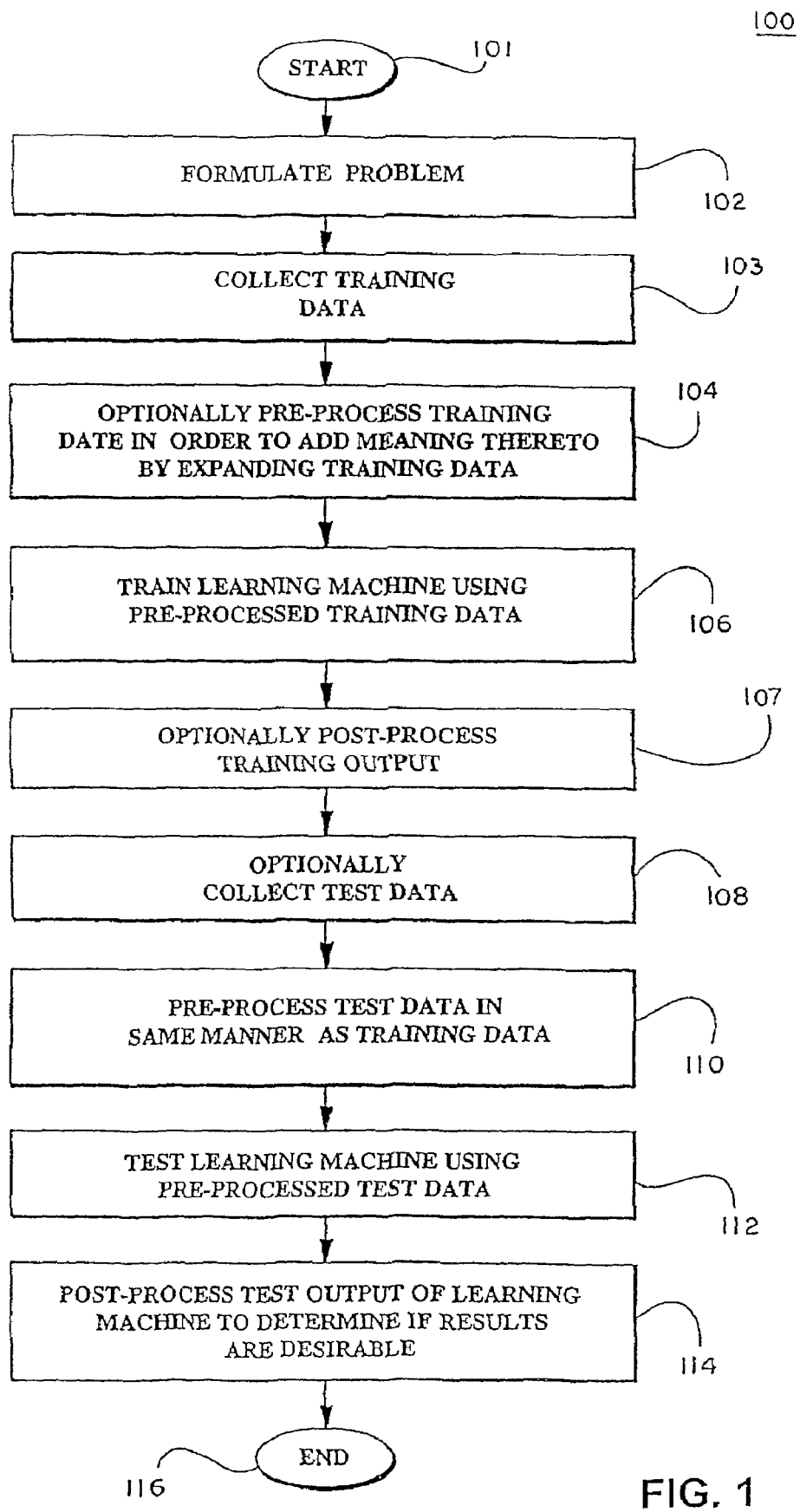
FIG. 1 is a flowchart illustrating an exemplary general method for increasing knowledge that may be discovered from data using a learning machine.

As used herein, "biological data" means any data derived from measuring biological conditions of human, animals or other biological organisms including microorganisms, viruses, plants and other living organisms. The measurements may be made by any tests, assays or observations that are known to physicians, scientists, diagnosticians, or the like. Biological data may include, but is not limited to, clinical tests and observations, physical and chemical measurements, genomic determinations, proteomic determinations, drug levels, hormonal and immunological tests, neurochemical or neurophysical measurements, mineral and vitamin level determinations, genetic and familial histories, and other determinations that may give insight into the state of the individual or individuals that are undergoing testing. The term "data" is used interchangeably with "biological data".

While several examples of learning machines exist and advancements are expected in this field, the exemplary embodiments of the present invention focus on kernel-based learning machines and more particularly on the support vector machine.

The present invention can be used to analyze biological data generated at multiple stages of investigation into biological functions, and further, to integrate the different kinds of data for novel diagnostic and prognostic determinations. For example, biological data obtained from clinical case information, such as diagnostic test data, family or genetic histories, prior or current medical treatments and the clinical outcomes of such activities, and published medical literature, can be utilized in the method and system of the present invention. Additionally, clinical samples such as diseased tissues or fluids, and normal tissues and fluids, and cell separations can provide biological data that can be utilized by the current invention. Proteomic determinations such as 2-D gel, mass spectrophotometry and antibody screening can be used to establish databases that can be utilized by the present invention. Genomic databases can also be used alone or in combination with the above-described data and databases by the present invention to provide comprehensive diagnosis, prognosis or predictive capabilities to the user of the present invention.

A first aspect of the present invention facilitates analysis of data by pre-processing the data prior to using the data to train a learning machine and/or optionally post-processing the output from a learning machine. Generally stated, pre-processing data comprises reformatting or augmenting the data in order to allow the learning machine to be applied most advantageously. More specifically, pre-processing involves selecting a method for reducing the dimensionality of the feature space, i.e., selecting the features which best represent the data. In the preferred embodiment, recursive feature elimination (RFE) is used, however, other methods may be used to select an optimal subset of features, such as those disclosed in co-pending PCT application Serial No. PCT/US02/16012, filed in the U.S. Receiving Office on May 20, 2002, entitled "Methods for Feature Selection in a Learning Machine", which is incorporated herein by reference. The features remaining after feature selection are then used to train a learning machine for purposes of pattern classification, regression, clustering and/or novelty detection.

In a manner similar to pre-processing, post-processing involves interpreting the output of a learning machine in order to discover meaningful characteristics thereof. The meaningful characteristics to be ascertained from the output may be problem- or data-specific. Post-processing involves interpreting the output into a form that, for example, may be understood by or is otherwise useful to a human observer, or converting the output into a form which may be readily received by another device for, e.g., archival or transmission.

FIG. 1 is a flowchart illustrating a general method 100 for analyzing data using learning machines. The method 100 begins at starting block 101 and progresses to step 102 where a specific problem is formalized for application of analysis through machine learning. Particularly important is a proper formulation of the desired output of the learning machine. For instance, in predicting future performance of an individual equity instrument, or a market index, a learning machine is likely to achieve better performance when predicting the expected future change rather than predicting the future price level. The future price expectation can later be derived in a post-processing step as will be discussed later in this specification.

After problem formalization, step 103 addresses training data collection. Training data comprises a set of data points having known characteristics. This data may come from customers, research facilities, academic institutions, national laboratories, commercial entities or other public or confidential sources. The source of the data and the types of data provided are not crucial to the methods. Training data may be collected from one or more local and/or remote sources. The data may be provided through any means such as via the internet, server linkages or discs, CD/ROMs, DVDs or other storage means. The collection of training data may be accomplished manually or by way of an automated process, such as known electronic data transfer methods. Accordingly, an exemplary embodiment of the learning machine for use in conjunction with the present invention may be implemented in a networked computer environment. Exemplary operating environments for implementing various embodiments of the learning machine will be described in detail with respect to FIGS. 4-5.

At step 104, the collected training data is optionally pre-processed in order to allow the learning machine to be applied most advantageously toward extraction of the knowledge inherent to the training data. During this preprocessing stage a variety of different transformations can be performed on the data to enhance its usefulness. Such transformations, examples of which include addition of expert information, labeling, binary conversion, Fourier transformations, etc., will be readily apparent to those of skill in the art. However, the preprocessing of interest in the present invention is the reduction of dimensionality by way of feature selection, different methods of which are described in detail below.

Returning to FIG. 1, an exemplary method 100 continues at step 106, where the learning machine is trained using the pre-processed data. As is known in the art, a learning machine is trained by adjusting its operating parameters until a desirable training output is achieved. The determination of whether a training output is desirable may be accomplished either manually or automatically by comparing the training output to the known characteristics of the training data. A learning machine is considered to be trained when its training output is within a predetermined error threshold from the known characteristics of the training data. In certain situations, it may be desirable, if not necessary, to post-process the training output of the learning machine at step 107. As mentioned, post-processing the output of a learning machine involves interpreting the output into a meaningful form. In the context of a regression problem, for example, it may be necessary to determine range categorizations for the output of a learning machine in order to determine if the input data points were correctly categorized. In the example of a pattern recognition problem, it is often not necessary to post-process the training output of a learning machine.

At step 108, test data is optionally collected in preparation for testing the trained learning machine. Test data may be collected from one or more local and/or remote sources. In practice, test data and training data may be collected from the same source(s) at the same time. Thus, test data and training data sets can be divided out of a common data set and stored in a local storage medium for use as different input data sets for a learning machine. Regardless of how the test data is collected, any test data used must be pre-processed at step 110 in the same manner as was the training data. As should be apparent to those skilled in the art, a proper test of the learning may only be accomplished by using testing data of the same format as the training data. Then, at step 112 the learning machine is tested using the pre-processed test data, if any. The test output of the learning machine is optionally post-processed at step 114 in order to determine if the results are desirable. Again, the post processing step involves interpreting the test output into a meaningful form. The meaningful form may be one that is readily understood by a human or one that is compatible with another processor. Regardless, the test output must be post-processed into a form which may be compared to the test data to determine whether the results were desirable. Examples of post-processing steps include but are not limited of the following: optimal categorization determinations, scaling techniques (linear and non-linear), transformations (linear and non-linear), and probability estimations. The method 100 ends at step 116.

Figure 2:
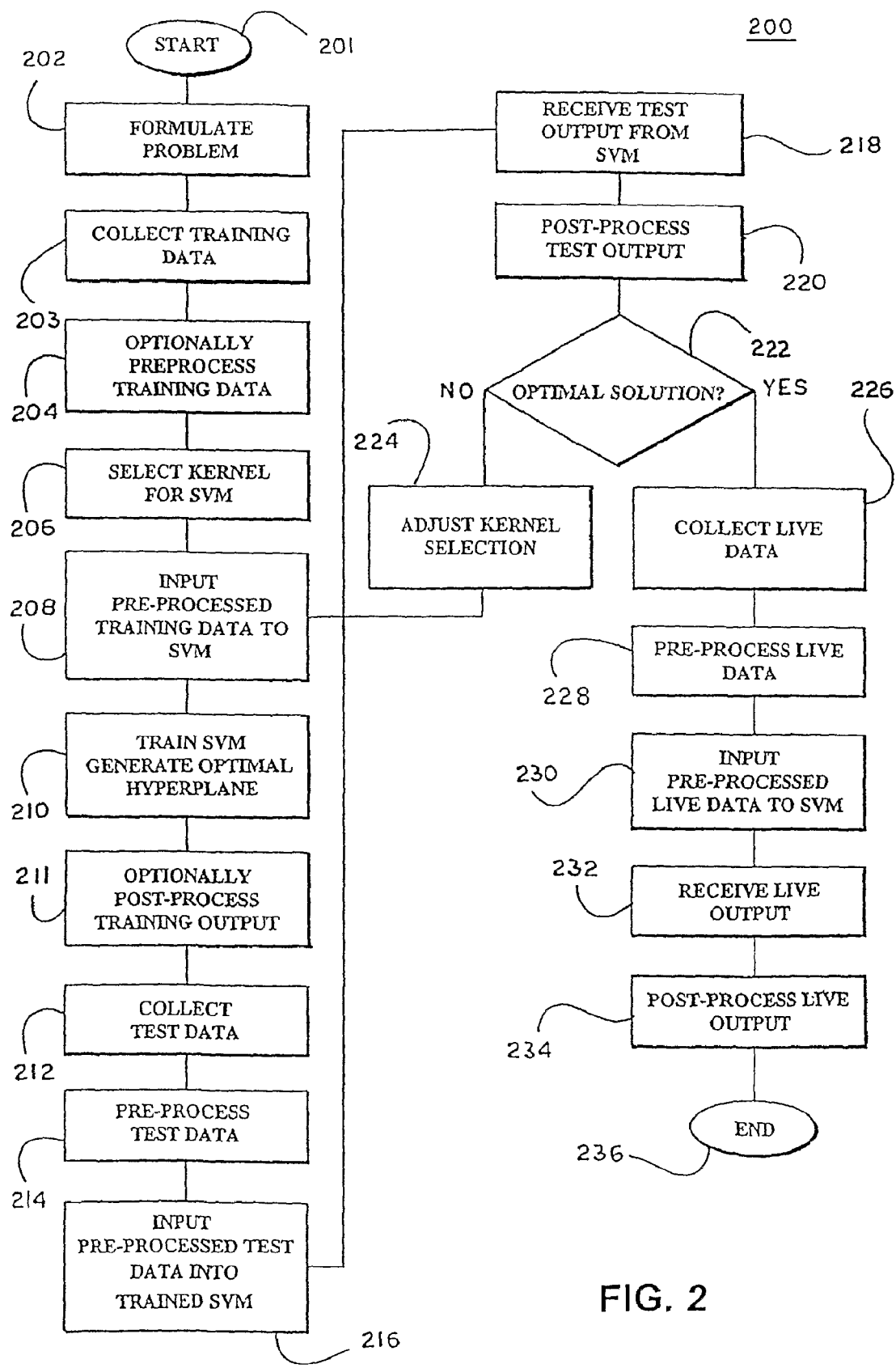
FIG. 2 is a flowchart illustrating an exemplary method for increasing knowledge that may be discovered from data using a support vector machine.

FIG. 2 is a flow chart illustrating an exemplary method 200 for enhancing knowledge that may be discovered from data using a specific type of learning machine known as a support vector machine (SVM). A SVM implements a specialized algorithm for providing generalization when estimating a multi-dimensional function from a limited collection of data. A SVM may be particularly useful in solving dependency estimation problems. More specifically, a SVM may be used accurately in estimating indicator functions (e.g. pattern recognition problems) and real-valued functions (e.g. function approximation problems, regression estimation problems, density estimation problems, and solving inverse problems). The SVM was originally developed by Boser, Guyon and Vapnik ("A training algorithm for optimal margin classifiers", *Fifth Annual Workshop on Computational Learning Theory*, Pittsburgh, ACM (1992) pp. 142-152). The concepts underlying the SVM are also explained in detail in Vapnik's book, entitled *Statistical Learning Theory* (John Wiley & Sons, Inc. 1998), which is herein incorporated by reference in its entirety. Accordingly, a familiarity with SVMs and the terminology used therewith are presumed throughout this specification.

The exemplary method 200 begins at starting block 201 and advances to step 202, where a problem is formulated and then to step 203, where a training data set is collected. As was described with reference to FIG. 1, training data may be collected from one or more local and/or remote sources, through a manual or automated process. At step 204 the training data is optionally pre-processed. Those skilled in the art should appreciate that SVMs are capable of processing input data having extremely large dimensionality, however, according to the present invention, pre-processing includes the use of feature selection methods to reduce the dimensionality of feature space.

At step 206 a kernel is selected for the SVM. As is known in the art, different kernels will cause a SVM to produce varying degrees of quality in the output for a given set of input data. Therefore, the selection of an appropriate kernel may be essential to the desired quality of the output of the SVM. In one embodiment of the learning machine, a kernel may be chosen based on prior performance knowledge. As is known in the art, exemplary kernels include polynomial kernels, radial basis classifier kernels, linear kernels, etc. In an alternate embodiment, a customized kernel may be created that is specific to a particular problem or type of data set. In yet another embodiment, the multiple SVMs may be trained and tested simultaneously, each using a different kernel. The quality of the outputs for each simultaneously trained and tested SVM may be compared using a variety of selectable or weighted metrics (see step 222) to determine the most desirable kernel.

Next, at step 208 the pre-processed training data is input into the SVM. At step 210, the SVM is trained using the pre-processed training data to generate an optimal hyperplane. Optionally, the training output of the SVM may then be post-processed at step 211. Again, post-processing of training output may be desirable, or even necessary, at this point in order to properly calculate ranges or categories for the output. At step 212 test data is collected similarly to previous descriptions of data collection. The test data is pre-processed at step 214 in the same manner as was the training data above. Then, at step 216 the pre-processed test data is input into the SVM for processing in order to determine whether the SVM was trained in a desirable manner. The test output is received from the SVM at step 218 and is optionally post-processed at step 220.

Based on the post-processed test output, it is determined at step 222 whether an optimal minimum was achieved by the SVM. Those skilled in the art should appreciate that a SVM is operable to ascertain an output having a global minimum error. However, as mentioned above, output results of a SVM for a given data set will typically vary with kernel selection. Therefore, there are in fact multiple global minimums that may be ascertained by a SVM for a given set of data. As used herein, the term "optimal minimum" or "optimal solution" refers to a selected global minimum that is considered to be optimal (e.g. the optimal solution for a given set of problem specific, pre-established criteria) when compared to other global minimums ascertained by a SVM. Accordingly, at step 222, determining whether the optimal minimum has been ascertained may involve comparing the output of a SVM with a historical or predetermined value. Such a predetermined value may be dependant on the test data set. For example, in the context of a pattern recognition problem where data points are classified by a SVM as either having a certain characteristic or not having the characteristic, a global minimum error of 50% would not be optimal. In this example, a global minimum of 50% is no better than the result that would be achieved by flipping a coin to determine whether the data point had that characteristic. As another example, in the case where multiple SVMs are trained and tested simultaneously with varying kernels, the outputs for each SVM may be compared with output of other SVM to determine the practical optimal solution for that particular set of kernels. The determination of whether an optimal solution has been ascertained may be performed manually or through an automated comparison process.

If it is determined that the optimal minimum has not been achieved by the trained SVM, the method advances to step 224, where the kernel selection is adjusted. Adjustment of the kernel selection may comprise selecting one or more new kernels or adjusting kernel parameters. Furthermore, in the case where multiple SVMs were trained and tested simultaneously, selected kernels may be replaced or modified while other kernels may be re-used for control purposes. After the kernel selection is adjusted, the method 200 is repeated from step 208, where the pre-processed training data is input into the SVM for training purposes. When it is determined at step 222 that the optimal minimum has been achieved, the method advances to step 226, where live data is collected similarly as described above. By definition, live data has not been previously evaluated, so that the desired output characteristics that were known with respect to the training data and the test data are not known.

At step 228 the live data is pre-processed in the same manner as was the training data and the test data. At step 230, the live pre-processed data is input into the SVM for processing. The live output of the SVM is received at step 232 and is post-processed at step 234. The method 200 ends at step 236.

Figure 3:
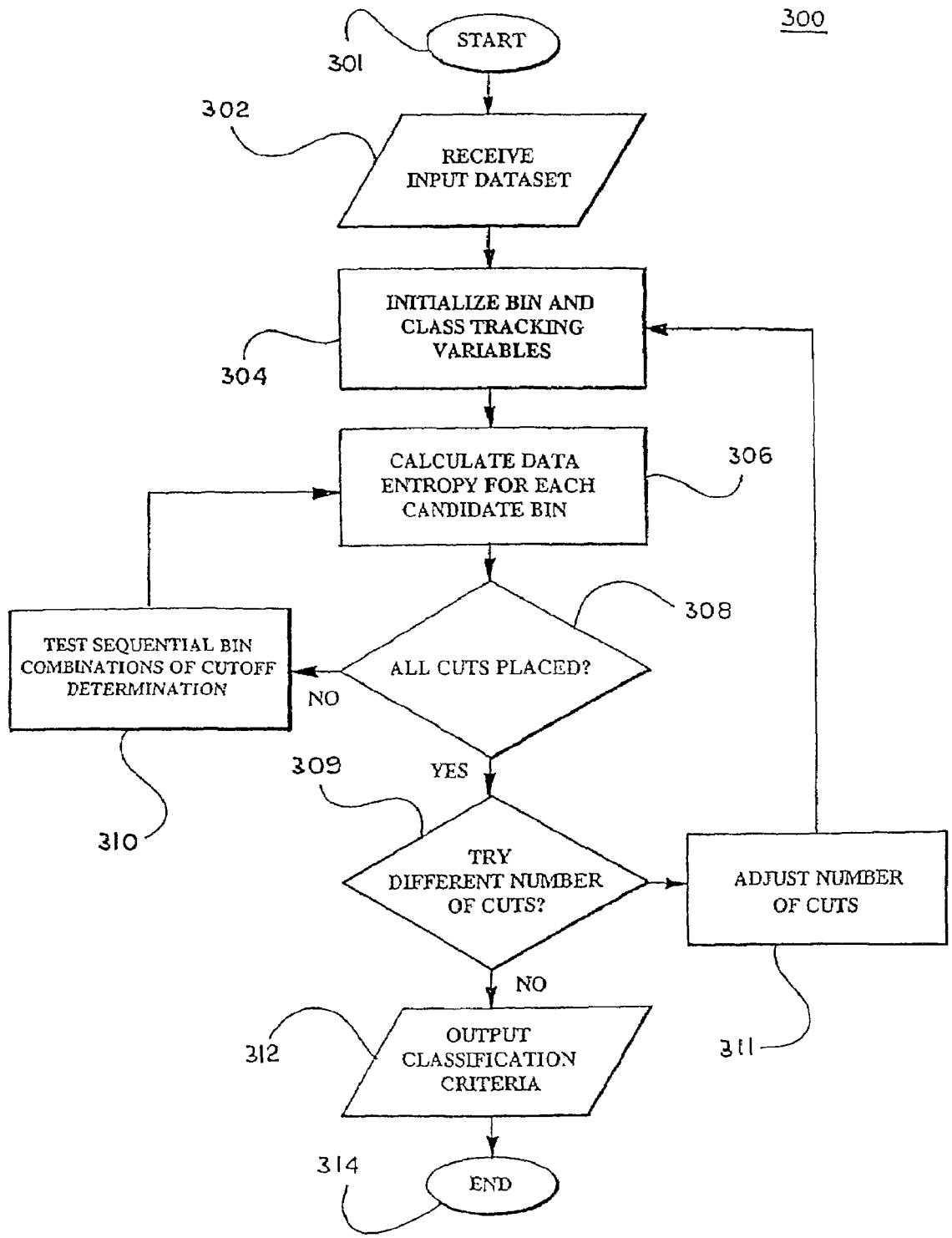
FIG. 3 is a flowchart illustrating an exemplary optimal categorization method that may be used in a stand-alone configuration or in conjunction with a learning machine for pre-processing or post-processing techniques in accordance with an exemplary embodiment of the present invention.

FIG. 3 is a flow chart illustrating an exemplary optimal categorization method 300 that may be used for pre-processing data or post-processing output from a learning machine. Additionally, as will be described below, the exemplary optimal categorization method may be used as a stand-alone categorization technique, independent from learning machines. The exemplary optimal categorization method 300 begins at starting block 301 and progresses to step 302, where an input data set is received. The input data set comprises a sequence of data samples from a continuous variable. The data samples fall within two or more classification categories. Next, at step 304 the bin and class-tracking variables are initialized. As is known in the art, bin variables relate to resolution, while class-tracking variables relate to the number of classifications within the data set. Determining the values for initialization of the bin and class-tracking variables may be performed manually or through an automated process, such as a computer program for analyzing the input data set. At step 306, the data entropy for each bin is calculated. Entropy is a mathematical quantity that measures the uncertainty of a random distribution. In the exemplary method 300, entropy is used to gauge the gradations of the input variable so that maximum classification capability is achieved.

The method 300 produces a series of "cuts" on the continuous variable, such that the continuous variable may be divided into discrete categories. The cuts selected by the exemplary method 300 are optimal in the sense that the average entropy of each resulting discrete category is minimized. At step 308, a determination is made as to whether all cuts have been placed within input data set comprising the continuous variable. If all cuts have not been placed, sequential bin combinations are tested for cutoff determination at step 310. From step 310, the exemplary method 300 loops back through step 306 and returns to step 308 where it is again determined whether all cuts have been placed within input data set comprising the continuous variable. When all cuts have been placed, the entropy for the entire system is evaluated at step 309 and compared to previous results from testing more or fewer cuts. If it cannot be concluded that a minimum entropy state has been determined, then other possible cut selections must be evaluated and the method proceeds to step 311. From step 311*a* heretofore untested selection for number of cuts is chosen and the above process is repeated from step 304. When either the limits of the resolution determined by the bin width has been tested or the convergence to a minimum solution has been identified, the optimal classification criteria is output at step 312 and the exemplary optimal categorization method 300 ends at step 314.

The optimal categorization method 300 takes advantage of dynamic programming techniques. As is known in the art, dynamic programming techniques may be used to significantly improve the efficiency of solving certain complex problems through carefully structuring an algorithm to reduce redundant calculations. In the optimal categorization problem, the straightforward approach of exhaustively searching through all possible cuts in the continuous variable data would result in an algorithm of exponential complexity and would render the problem intractable for even moderate sized inputs. By taking advantage of the additive property of the target function, in this problem the average entropy, the problem may be divide into a series of sub-problems. By properly formulating algorithmic sub-structures for solving each sub-problem and storing the solutions of the sub-problems, a significant amount of redundant computation may be identified and avoided. As a result of using the dynamic programming approach, the exemplary optimal categorization method 300 may be implemented as an algorithm having a polynomial complexity, which may be used to solve large sized problems.

As mentioned above, the exemplary optimal categorization method 300 may be used in pre-processing data and/or post-processing the output of a learning machine. For example, as a pre-processing transformation step, the exemplary optimal categorization method 300 may be used to extract classification information from raw data. As a post-processing technique, the exemplary optimal range categorization method may be used to determine the optimal cut-off values for markers objectively based on data, rather than relying on ad hoc approaches. As should be apparent, the exemplary optimal categorization method 300 has applications in pattern recognition, classification, regression problems, etc. The exemplary optimal categorization method 300 may also be used as a stand-alone categorization technique, independent from SVMs and other learning machines.

Figure 4:
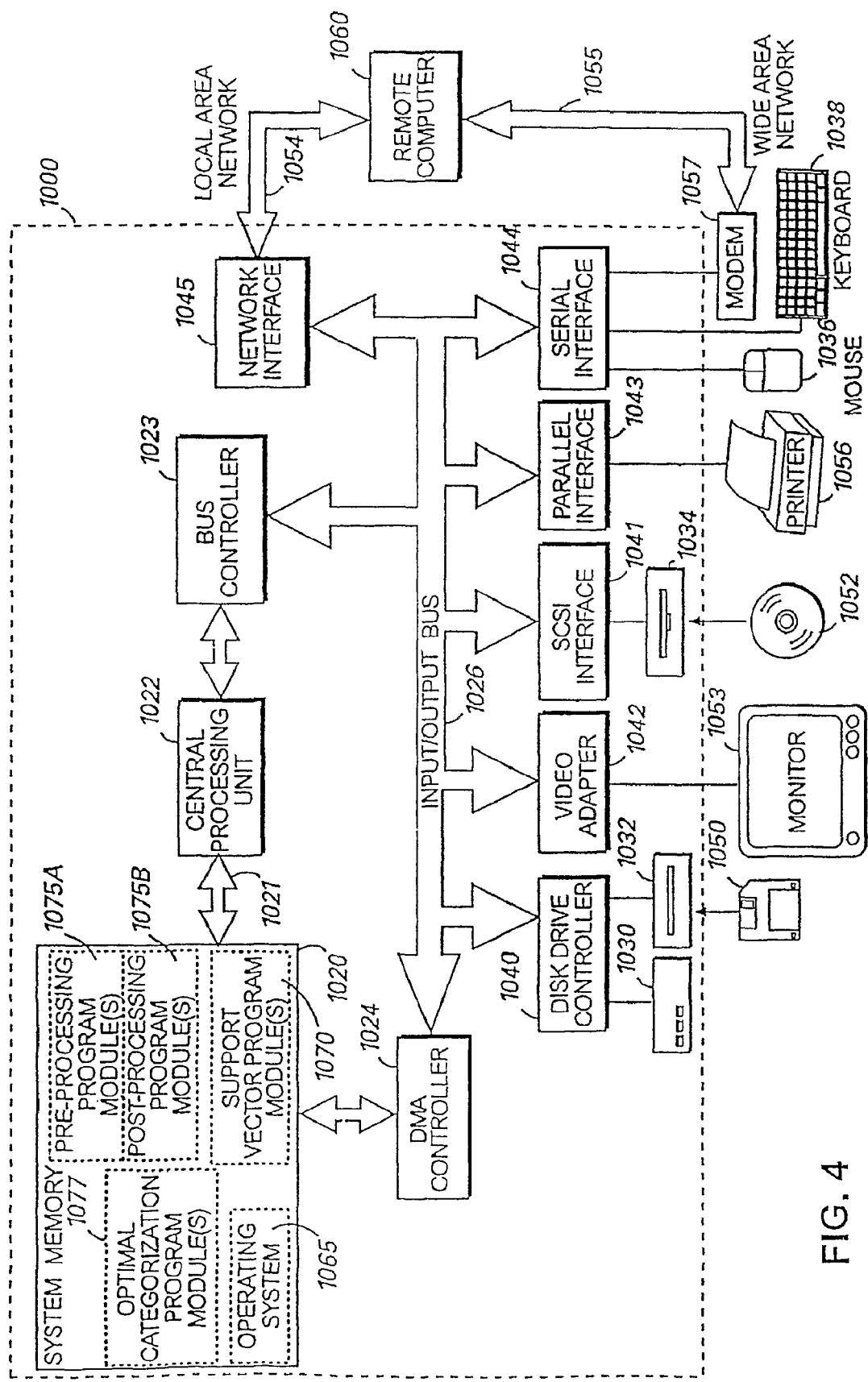
FIG. 4 is a functional block diagram illustrating an exemplary operating environment for an embodiment of the present invention.

FIG. 4 and the following discussion are intended to provide a brief and general description of a suitable computing environment for implementing biological data analysis according to the present invention. Although the system shown in FIG. 4 is a conventional personal computer 1000, those skilled in the art will recognize that the invention also may be implemented using other types of computer system configurations. The computer 1000 includes a central processing unit 1022, a system memory 1020, and an Input/Output ("I/O") bus 1026. A system bus 1021 couples the central processing unit 1022 to the system memory 1020. A bus controller 1023 controls the flow of data on the I/O bus 1026 and between the central processing unit 1022 and a variety of internal and external I/O devices. The I/O devices connected to the I/O bus 1026 may have direct access to the system memory 1020 using a Direct Memory Access ("DMA") controller 1024.

The I/O devices are connected to the I/O bus 1026 via a set of device interfaces. The device interfaces may include both hardware components and software components. For instance, a hard disk drive 1030 and a floppy disk drive 1032 for reading or writing removable media 1050 may be connected to the I/O bus 1026 through disk drive controllers 1040. An optical disk drive 1034 for reading or writing optical media 1052 may be connected to the I/O bus 1026 using a Small Computer System Interface ("SCSI") 1041. Alternatively, an IDE (Integrated Drive Electronics, i.e., a hard disk drive interface for PCs), ATAPI (ATtAchment Packet Interface, i.e., CD-ROM and tape drive interface), or EIDE (Enhanced IDE) interface may be associated with an optical drive such as may be the case with a CD-ROM drive. The drives and their associated computer-readable media provide nonvolatile storage for the computer 1000. In addition to the computer-readable media described above, other types of computer-readable media may also be used, such as ZIP drives, or the like.

A display device 1053, such as a monitor, is connected to the I/O bus 1026 via another interface, such as a video adapter 1042. A parallel interface 1043 connects synchronous peripheral devices, such as a laser printer 1056, to the I/O bus 1026.

A serial interface 1044 connects communication devices to the I/O bus 1026. A user may enter commands and information into the computer 1000 via the serial interface 1044 or by using an input device, such as a keyboard 1038, a mouse 1036 or a modem 1057. Other peripheral devices (not shown) may also be connected to the computer 1000, such as audio input/output devices or image capture devices.

A number of program modules may be stored on the drives and in the system memory 1020. The system memory 1020 can include both Random Access Memory ("RAM") and Read Only Memory ("ROM"). The program modules control how the computer 1000 functions and interacts with the user, with I/O devices or with other computers. Program modules include routines, operating systems 1065, application programs, data structures, and other software or firmware components. In an illustrative embodiment, the learning machine may comprise one or more pre-processing program modules 1075A, one or more post-processing program modules 1075B, and/or one or more optimal categorization program modules 1077 and one or more SVM program modules 1070 stored on the drives or in the system memory 1020 of the computer 1000. Specifically, pre-processing program modules 1075A, post-processing program modules 1075B, together with the SVM program modules 1070 may comprise computer-executable instructions for pre-processing data and post-processing output from a learning machine and implementing the learning algorithm according to the exemplary methods described with reference to FIGS. 1 and 2. Furthermore, optimal categorization program modules 1077 may comprise computer-executable instructions for optimally categorizing a data set according to the exemplary methods described with reference to FIG. 3.

The computer 1000 may operate in a networked environment using logical connections to one or more remote computers, such as remote computer 1060. The remote computer 1060 may be a server, a router, a peer device or other common network node, and typically includes many or all of the elements described in connection with the computer 1000. In a networked environment, program modules and data may be stored on the remote computer 1060. The logical connections depicted in FIG. 4 include a local area network ("LAN") 1054 and a wide area network ("WAN") 1055. In a LAN environment, a network interface 1045, such as an Ethernet adapter card, can be used to connect the computer 1000 to the remote computer 1060. In a WAN environment, the computer 1000 may use a telecommunications device, such as a modem 1057, to establish a connection. It will be appreciated that the network connections shown are illustrative and other devices of establishing a communications link between the computers may be used.

In another embodiment, a plurality of SVMs can be configured to hierarchically process multiple data sets in parallel or sequentially. In particular, one or more first-level SVMs may be trained and tested to process a first type of data and one or more first-level SVMs can be trained and tested to process a second type of data. Additional types of data may be processed by other first-level SVMs. The output from some or all of the first-level SVMs may be combined in a logical manner to produce an input data set for one or more second-level SVMs. In a similar fashion, output from a plurality of second-level SVMs may be combined in a logical manner to produce input data for one or more third-level SVM. The hierarchy of SVMs may be expanded to any number of levels as may be appropriate. In this manner, lower hierarchical level SVMs may be used to pre-process data that is to be input into higher level SVMs. Also, higher hierarchical level SVMs may be used to post-process data that is output from lower hierarchical level SVMs.

Each SVM in the hierarchy or each hierarchical level of SVMs may be configured with a distinct kernel. For example, SVMs used to process a first type of data may be configured with a first type of kernel while SVMs used to process a second type of data may utilize a second, different type of kernel. In addition, multiple SVMs in the same or different hierarchical level may be configured to process the same type of data using distinct kernels.

Figure 5:
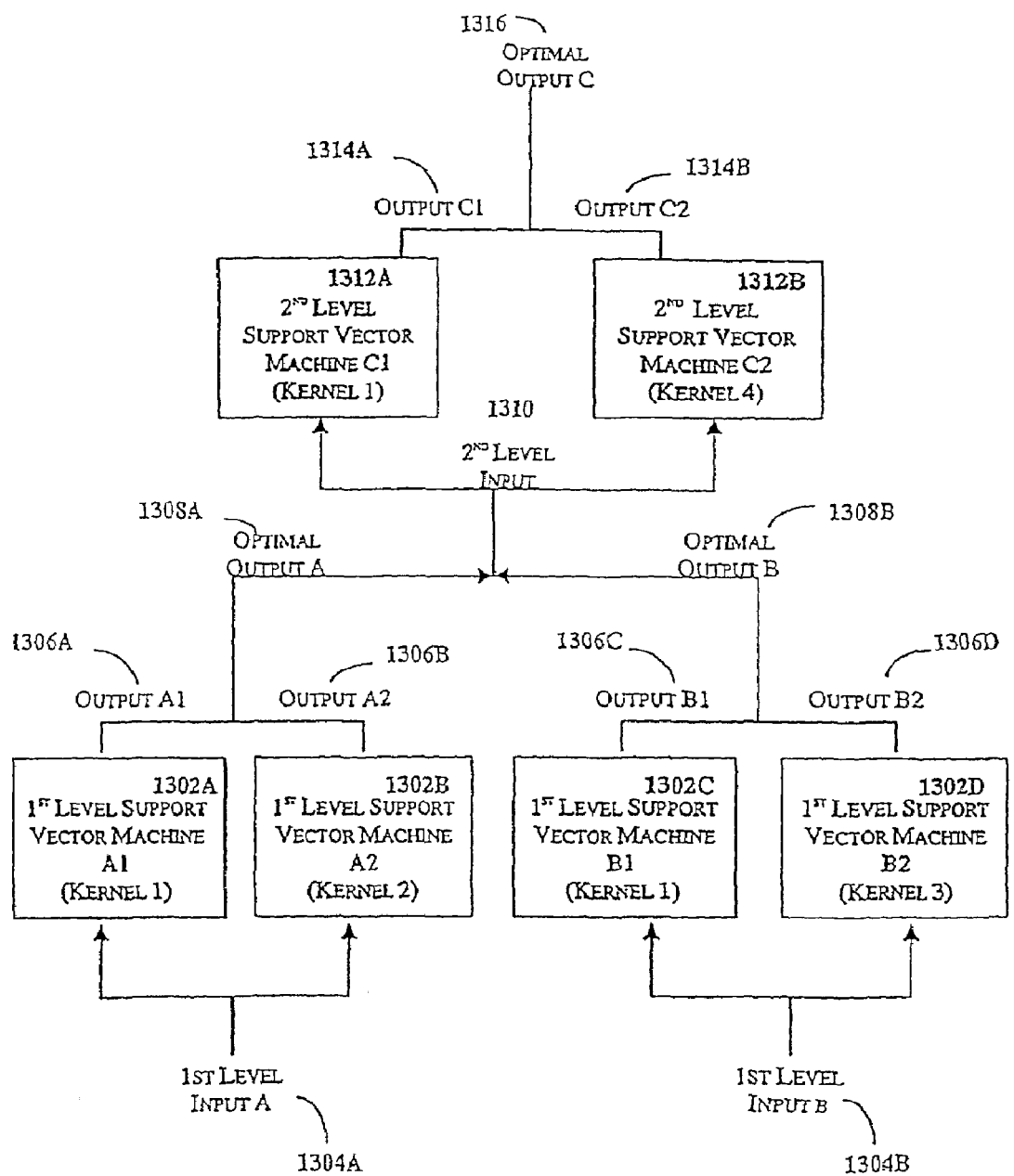
FIG. 5 is a functional block diagram illustrating a hierarchical system of multiple support vector machines.

FIG. 5 illustrates an exemplary hierarchical system of SVMs. As shown, one or more first-level SVMs 1302a and 1302b may be trained and tested to process a first type of input data 1304a, such as mammography data, pertaining to a sample of medical patients. One or more of these SVMs may comprise a distinct kernel, indicated as "KERNEL 1" and "KERNEL 2". Also, one or more additional first-level SVMs 1302c and 1302d may be trained and tested to process a second type of data 1304b, which may be, for example, genomic data for the same or a different sample of medical patients. Again, one or more of the additional SVMs may comprise a distinct kernel, indicated as "KERNEL 1" and "KERNEL 3". The output from each of the like first-level SVMs may be compared with each other, e.g., 1306a compared with 1306b; 1306c compared with 1306d, in order to determine optimal outputs 1308a and 1308b. Then, the optimal outputs from the two groups or first-level SVMs, i.e., outputs 1308a and 1308b, may be combined to form a new multi-dimensional input data set 1310, for example, relating to mammography and genomic data. The new data set may then be processed by one or more appropriately trained and tested second-level SVMs 1312a and 1312b. The resulting outputs 1314a and 1314b from second-level SVMs 1312a and 1312b may be compared to determine an optimal output 1316. Optimal output 1316 may identify causal relationships between the mammography and genomic data points. As should be apparent to those of skill in the art, other combinations of hierarchical SVMs may be used to process either in parallel or serially, data of different types in any field or industry in which analysis of data is desired.

Figure 6:
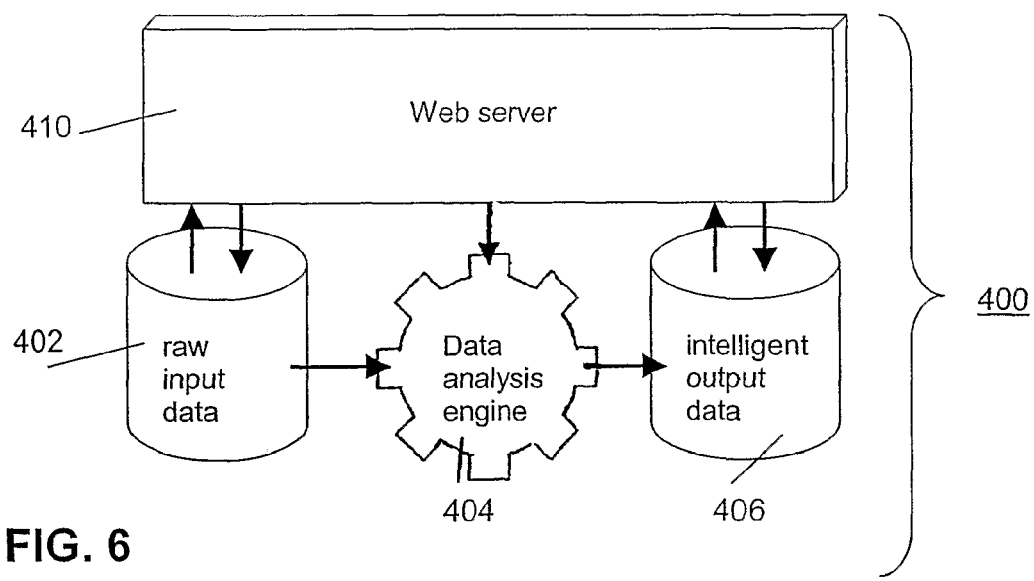
FIG. 6 is a block diagram of the generic architecture of a module of the data mining platform.

FIG. 6 illustrates the general architecture of a module 400 of the data mining platform of the present invention. The central component of module 400 is the data analysis engine 404, which, in the preferred embodiment is one or more SVMs. The analysis engine 404 processes raw input data from input database 402 to produce intelligent output data at output database 406. A web server 410 offers an interface to view the data and monitor the engine. Raw input data may be unstructured or weakly structured, and may be in the form of, for example, sequences of characters or a table of coefficients. Output data are more structured and typically are in the form of graphs, e.g., decision trees, networks, nested subsets, or ranked lists.

Figure 7:
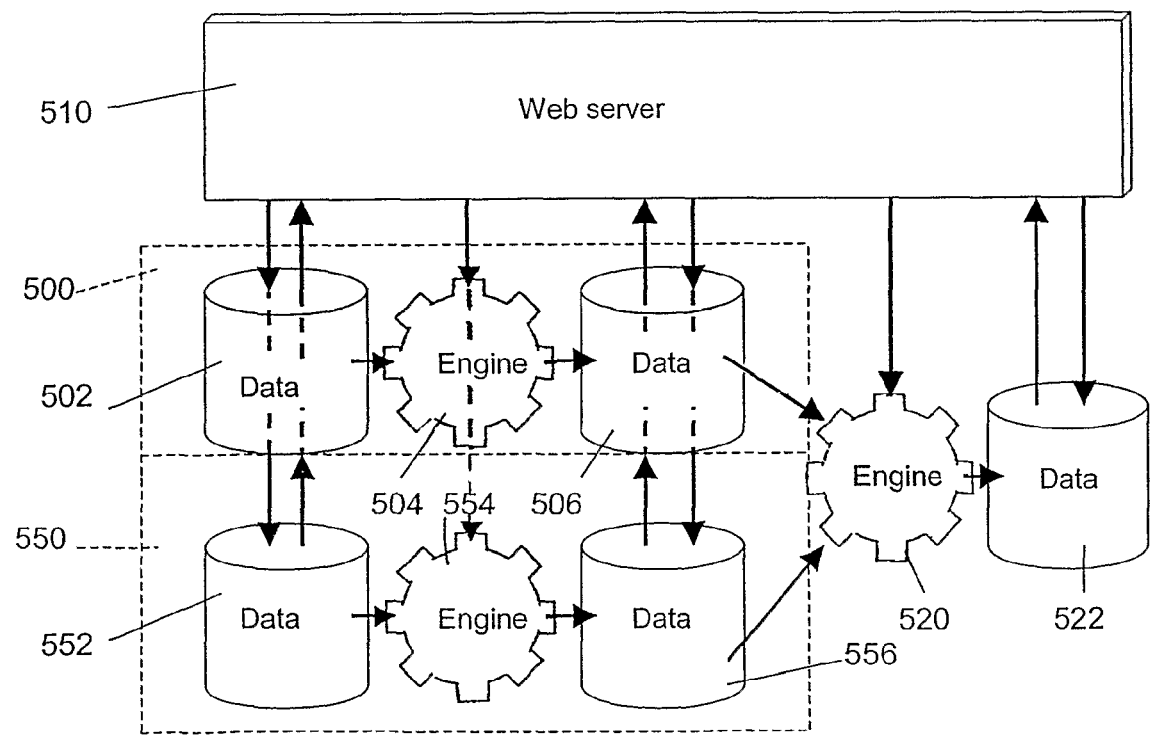
FIG. 7 is a block diagram of an exemplary embodiment of the data mining platform having two modules for processing, then combining, two different kinds of input data.

The basic building block of the module comprises a web interface to a software package (written in scientific language such as MatLab®, a scripting language such as Perl, or a programming language such as C or C++) and databases holding input data and the results of the computation, i.e., output data. A wizard program guides the researcher through a deployment procedure. A key aspect of this system is its modularity, which allows the assembly of modules for processing heterogeneous data sets in a hierarchical structure, or modules may be cascaded. As illustrated in FIG. 7, two modules 500 and 550 each possess the basic module components of the input database 502, 552, the data analysis engine 504, 554 and the output database 506, 556. (Note that the web server 510 is not shown within the dashed lines used to indicate each module because it is shared by the two modules.) An additional data analysis engine 520 is provided to receive, combine and process the outputs of the two modules 500 and 550. The results of this second analysis operation are then provided to output database 522. As indicated in the drawing, each component of each module 500, 550, the second analysis engine 520 and the second output database 522 are in communication with the web server 510 to provide for viewing and monitoring.

The essential difference between any two modules within the platform resides in the type of information each one processes. For example, one module may process numerical or structured data, while another might process textual or unstructured data. Both modules rely on the same architecture and require equally powerful matching learning and statistical techniques for data analysis and data mining.

In a first exemplary embodiment, the basic module is an enterprise server application accessible from a regular Internet Web browser. Its purpose is to offer on-line access to numerical simulations through a user-friendly interface. There are four main functions. First is the computer engine monitor, in which a user can set parameters, input raw data, and order a new batch of numerical experiments. Second is the data explorer, through which the user can recall the results of numerical experiments and view them in text and/or graphical format. Third are general administrative services and infrastructure which provide for pre- and post-login screens. Fourth is a wizard program that guides the researcher through a deployment procedure to upload new software modules. The module server is a restricted area accessible only by the server operator and authorized customers and guests. Data transmission between the browser and server is encrypted (HTTPS protocol) and user authentication through a login password combination is required to enter the site. The server is preferably protected behind a firewall to protect the operator's network. Access may be divided into categories, with different levels of access according to the user's category.

In the preferred embodiment, the module server is implemented in Java™ and adopts Sun Microsystems' specification of the Java 2 Platform, Enterprise Edition ("J2EE"). This platform is an architecture for developing, deploying and executing applications in a distributed environment. These applications require system-level services, such as transaction management, security, client connectivity, and database access. The primary benefits of Java and J2EE include power of expression of object-oriented coding; ease of implementation, deployment and maintenance; clean, modular and scalable architecture; distributed application across processes and machines; code portability across different operating systems and different J2EE platform vendors.

An important exception to implementation of the module using Java is that the data analysis engine at the core of the module will preferably be implemented using C, or will be executed inside a third-party environment such as MatLab®. For increased efficiency, the engine processes can be hosted in a dedicated, extra-powered machine.

The J2EE platform is thus reserved for the high-level control of the workflow, whereas low-level computation intensive tasks are performed outside of the Java environment.

Figure 8:
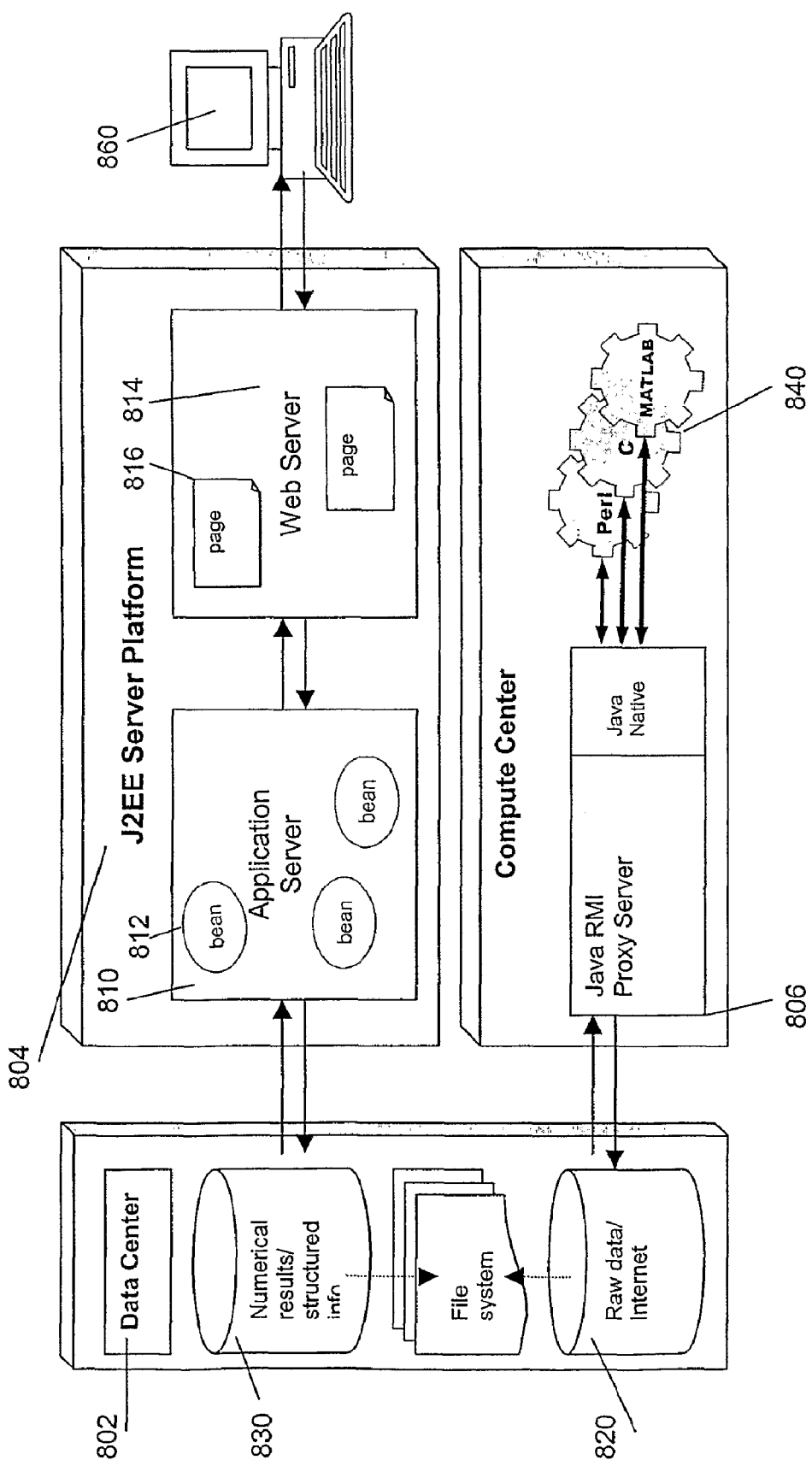
FIG. 8 is a block diagram of the global architecture of a module of the data mining platform.

FIG. 8 illustrates the global architecture of the basic module, with the input and output data being grouped into the "Data Center" 802. The main application is split into a server part, J2EE server platform 804 and a computational part, Compute Center 806.

The components of the Data Center 802 will vary depending on the type of data to be processed and generated. For example, in the case of gene expression data to be analyzed for diagnosing a disease, the input data 820 is raw data, and the output data 830 is numerical results. In the case of a search of published literature for information on gene-disease-organ relationships, the input data 820 is obtained from the a search of the Internet and the output data 830 is structured information.

In the J2EE application model, the "Java beans" 812 are the business objects that reside in the application server 810. "Java beans" typically contain the logic that operates on the data. Examples of beans for application to bioinformatics according to the present invention are gene datasets, gene tree results, patient records, documents, document search results, etc. The Web pages 816 are the business objects residing in the Web server 814. The application server 810 and the Web server 814 are the "containers" that contain the beans 812 and the pages 816, respectively. Connectors provide a low level infrastructure of communication between servers, clients and database systems using Java protocols such as Remote Method Invocation (RMI) and Java Database Connection (JDBC). The Computer Center 806 includes a Java RMI Proxy Server, the Java Native Interface and the analysis engines 840. For reasons of performance, the mathematical algorithms that reside in Compute Center 806, are preferably not implemented in Java. Instead, the analysis engine 840 is rather implemented in Perl, C or MatLab®. A front-end interface with the user is provided via a Web browser 860.

In summary, as shown in FIG. 8, the Web Browser 860 communicates with the Web Server 814, which in turn communicates with the Application Server 810, which in turn communicates with both Data Center 802 and Compute Center 806.

The components (beans 812 and pages 816) are the key focus of application developers, while system vendors implement containers and connectors to conceal complexity and promote portability. The component/container metaphor is pervasive across all levels of a computer organization, for example, application/operating system, Word® document/ word processor, Web page/Web browser, Java class byte code/Java virtual machine, etc. In each instance, a piece of logic (the component) is developed by a client user to be embedded in a larger environment provided by a vendor (the container) that is able to execute of view it.

The two subparts of the J2EE platform module 804 are the application server 810 and the Web server 814. The application server 810, is also known as the Enterprise Java Bean (EJB) Container. As is well known in the art, an EJB is defined as one component of a distributed transaction-oriented enterprise application. An enterprise bean typically contains business logic that operates on the enterprise's data, is created an managed at runtime by a container and can be included in an assembled application without requiring source code changes or recompilation. As it is well known in the art, the J2EE standard also distinguishes between two types of enterprise beans: "entity beans", the business objects that model and represent the data, and "session beans", the business objects that accesses and operates on the data. In the present invention, examples of entity beans include general services (User, CustomerAccount, DataAnalyst, etc.), genomics/microarray project (Gene, GeneDataSet, GeneTreeResults, etc, etc.), clinical project (Patient, ClinicalRecord, Provider, Procedure, HighCostResults, etc.), and information retrieval project (Document, Finding, BibReference, etc.). Examples of session beans include general services (SignIn, Admin, etc.) and, through their communication with the Data Center 802 (see FIG. 8), data access services (DataAccess, etc.).

Through their communication with the Compute Center 806, as shown in FIG. 8, session beans also carry over computation job requests, for example in a genomics/microarray project (GenesSVMSelector, etc.) a clinical project (HighCostPredictor, etc.), or an information retrieval project (DocumentFinder, etc.) Finally, through this same communication, session beans also support the deployment wizard that guides the researchers for uploading new software modules. Web server 814 is also known as the JavaServer Pages (JSP)/Servlet container. The J2EE server platform is well known in the art and, therefore, further explanation is not provided.

In an exemplary application to bioinformatics, the system according to the present invention provides for the following operations: 1) Data acquisition: For each event to be recorded (called a "pattern", which may correspond to a patient, a tissue, etc.) transform the inputs obtained by a sensor (such as a DNA microarray, a spectrometer) or transform textual information into a fixed dimension vector. The elements of the vector (called "features", input variables, components, or attributes) are computed from the data coming from the sensors or the text in a fixed determined way. The result of data acquisition is a matrix of patterns (lines) of features (columns), or vice versa. As previously stated, one module is provided for each type of data. 2) Preprocessing: Use a combination of normalization (e.g., subtracting mean and dividing by standard deviation) and non-linear filtering. Both the lines and the columns of the matrix may be normalized and filtered. These and other pre-processing operations are described below. 3) Baseline performance and data cleaning: Both manual and automatic cleaning of data are possible. The principle is to detect outliers that are difficult to predict with a learning machine. Details are provided below in the discussion of data cleaning algorithms.

4) Evaluate the problem dimensionality and difficulty: Use Principal Component Analysis (PCA), which is known in the art (see, e.g., Chapter 14 on "Kernel Feature Extraction" in *Learning with Kernels*, B. Schölkopf and A. J. Smola, 2002 MIT Press, which is incorporated herein by reference) to find the optimum number of principal components. Possible methods include, but are not limited to, using the gap statistic of Tishby et al. or by building a predictor. Attempt to build predictors with single genes. For classification, determine whether the problem is linearly separable with all genes and with single genes. Determine whether non-linear learning machines yield better leave-one-out performance on all genes and on the first few principal components. 5) Restrict the subset of methods to be further investigated: Given the analysis of problem dimensionality and difficulty, select a subset of learning machines with which to proceed (linear/non-linear, univariate with single gene ranking or multivariate with gene subset selection, e.g. RFE).

6) Run methods and generate plots of outer loop Cross Validation: Plot training and test performance as a function of number of genes to find the optimum number of genes; and plot training and test performance as a function of number of training examples for a given number of genes. Determine whether the data set size is sufficient to achieve asymptotic behavior. 7) Diagnose possible overfitting: If the multiple univariate methods give better results than the multivariate methods, it is possible that the multivariate feature selection method is overfitting. If overfitting of multivariate methods is diagnosed, try to improve performance by regularizing using clustering as a preprocessing operation and running gene selection on cluster centers. Other means of regularizing include restricting the RFE search to genes pre-selected by correlation methods or penalizing the removal of genes correlated with the ideal gene during RFE. (See the discussion below on RFE and pre-processing methods.) If no overfitting of multivariate methods is diagnosed, run supervised clustering of the remaining genes using as cluster centers the elements of the best gene subset and generate a tree of genes to provide alternate gene subsets. For purposes of efficiency, the tree may be built with the top best genes only.

8) Validate results using information retrieval: Calculate the relevance of genes to the disease at hand according to documents retrieved on-line. Compare the gene sets selected by various methods using such relevance criterion. Provide a tentative gene functional classification. 9) Combine the results obtained from data coming from various sources by combining the various feature structures obtained (tree, ranked lists, etc.) into a single structure. 10) Visualize the results: Display the results and let the user browse through the results and display for given features of the original information.

The following sections describe the various listed functions that are performed within the data mining platform according to the present invention.

Pre-processing Functions. Pre-processing can have a strong impact on SVM. In particular, feature scales must be comparable. A number of possible pre-processing methods may be used individually or in combination. One possible pre-processing method is to subtract the mean of a feature from each feature, then divide the result by its standard deviation. Such pre-processing is not necessary if scaling is taken into account in the computational cost function. Another pre-processing operation can be performed to reduce skew in the data distribution and provide more uniform distribution. This pre-processing step involves taking the log of the value, which is particularly advantageous when the data consists of gene expression coefficients, which are often obtained by computing the ratio of two values. For example, in a competitive hybridization scheme, DNA from two samples that are labeled differently are hybridized onto the array. One obtains at every point of the array two coefficients corresponding to the fluorescence of the two labels and reflecting the fraction of DNA of either sample that hybridized to the particular gene. Typically, the first initial preprocessing step that is taken is to take the ratio a/b of these two values. Although this initial preprocessing step is adequate, it may not be optimal when the two values are small. Other initial preprocessing steps include (a−b)/(a+b) and (log a−log b)/(log a+log b).

Another pre-processing step involves normalizing the data across all samples by subtracting the mean. This preprocessing step is supported by the fact that, using tissue samples, there are variations in experimental conditions from microarray to microarray. Although standard deviation seems to remain fairly constant, another possible preprocessing step was to divide the gene expression values by the standard deviation to obtain centered data of standardized variance.

To normalize each gene expression across multiple tissue samples, the mean expression value and standard deviation for each gene can be computed. For all the tissue sample values of that gene (training and test), that mean is then subtracted and the resultant value divided by the standard deviation. In some experiments, an additional preprocessing step can be added by passing the data through a squashing function to diminish the importance of the outliers.

In a variation on several of the preceding pre-processing methods, the data can be pre-processed by a simple "whitening" to make data matrix resemble "white noise." The samples can be pre-processed to: normalize matrix columns; normalize matrix lines; and normalize columns again. Normalization consists of subtracting the mean and dividing by the standard deviation. A further normalization step can be taken when the samples are split into a training set and a test set.

Clustering Methods: Because of data redundancy, it may be possible to find many subsets of data that provide a reasonable separation. To analyze the results, the relatedness of the data should be understand.

In correlation methods, the rank order characterizes how correlated the data is with the separation. Generally, a highly ranked data point taken alone provides a better separation than a lower ranked data point. It is therefore possible to set a threshold, e.g., keep only the top ranked data points, that separates "highly informative data points" from "less informative data points".

Feature selection methods such as SVM-RFE, described below, provide subsets of data that are both smaller and more discriminant. The data selection method using SVM-RFE also provides a ranked list of data. With this list, nested subsets of data of increasing sizes can be defined. However, the fact that one data point has a higher rank than another data point does not mean that this one factor alone characterizes the better separation. In fact, data that are eliminated in an early iteration could well be very informative but redundant with others that were kept. Data ranking allows for a building nested subsets of data that provide good separations, however it provides no information as to how good an individual data point may be.

Data ranking alone is insufficient to characterize which data points are informative and which ones are not, and also to determine which data points are complementary and which are redundant. Therefore, additional pre-processing in the form of clustering may be appropriate.

Feature ranking is often combined with clustering. One can obtain a ranked list of subsets of equivalent features by ranking the clusters. In one such method, a cluster can be replaced by its cluster center and scores can be computed for the cluster center. In another method, the features can be scored individually and the score of a cluster computed as the average score of the features in that cluster.

To overcome the problems of data ranking alone, the data can be preprocessed with an unsupervised clustering method. Using the $QT_{clust}$ ("quality clustering algorithm") algorithm, which is known in the art, particularly to those in the field of analysis of gene expression profiles, or some other clustering algorithm such as hierarchical clustering or SVM clustering, data can be grouped according to resemblance (according to a given metric). Cluster centers can then be used instead of data points themselves and processed by SVM-RFE to produce nested subsets of cluster centers. An optimum subset size can be chosen with the same cross-validation method used before.

Supervised clustering may be used to show specific clusters that have relevance for the specific knowledge being determined. For example, in analysis of gene expression data for diagnosis of colon cancer, a very large cluster of genes has been found that contained muscle genes that may be related to tissue composition and may not be relevant to the cancer vs. normal separation. Thus, these genes are good candidates for elimination from consideration as having little bearing on the diagnosis or prognosis for colon cancer.

Feature Selection The problem of selection of a small amount of data from a large data source, such as a gene subset from a microarray, is particularly solved using the methods, devices and systems described herein. Previous attempts to address this problem used correlation techniques, i.e., assigning a coefficient to the strength of association between variables. In examining genetic data to find determinative genes, these methods eliminate gene redundancy automatically and yield better and more compact gene subsets. The methods, devices and systems described herein can be used with publicly-available data to find relevant answers, such as genes determinative of a cancer diagnosis, or with specifically generated data.

The score of a feature is a quantity that measures the relevance or usefulness of that feature (or feature subset), with a larger score indicating that the feature is more useful or relevant. The problem of feature selection can only be well defined in light of the purpose of selecting a subset of features. Examples of feature selection problems that differ in their purpose include designing a diagnostic test that is economically viable. In this case, one may wish to find the smallest number of features that provides the smallest prediction error, or provides a prediction error less than a specified threshold. Another example is that of finding good candidate drug targets. The two examples differ in a number of ways.

In diagnosis and prognosis problems, the predictor cannot be dissociated from the problem because the ultimate goal is to provide a good predictor. One can refer to the usefulness of a subset of features to build a good predictor. The expected value of prediction error (the prediction error computed over an infinite number of test samples) would be a natural choice to derive a score. One problem is to obtain an estimate of the expected value of the prediction error of good precision by using only the available data. Another problem is that it is usually computationally impractical to build and test all the predictors corresponding to all possible subsets of features. As a result of these constraints, one typically resorts to use of sub-optimal scores in the search of good feature subsets.

In drug target selection, the predictor is only used to substitute the biological organism under study. For example, choosing subsets of genes and building new predictors are ways of substituting computer experiments for laboratory experiments that knock out genes and observe the consequence of the phenotype. The goal of target selection is to determine which feature(s) have the greatest impact on the health of the patient. The predictor itself is not going to be used. One refers to the "relevance" of the feature(s) with respect to the condition or phenotype under study. It may be a good idea to score features using multiple predictors and using a combined score to select features. Also, in diagnosis and prognosis, correlated features may be substituted for one another. The fact that feature correlations may mean causal relationships is not significant. On the other hand, in target selection, it is much more desirable to select the feature that is at the source of a cascade of events as opposed to a feature that is further down on the chain. For these reasons, designing a good score for target selection can be a complex problem.

In order to compare scores obtained from a number of different sources, and to allow simple score arithmatic, it is useful to normalize the scores. (See above discussion of pre-processing.) The ranking obtained with a given score is not affected by applying any monotonically increasing function. This includes exponentiation, multiplication or division by a positive constant, and addition or subtraction of a constant. Thus, a wide variety of normalization schemes may be applied.

As an example, the following considers conversion of scores into a quantity that can be interpreted as a probability or a degree of belief that a given feature or feature subset is "good". Assume that a given method generated scores for a family of subsets of features. Such family may include: all single features, all feature pairs, all possible subsets of features. Converting a score to a probability-like quantity may include exponentiation (to make the score positive), and normalization by dividing by the sum of all the scores in the family.

In the following, $P(f_1, f_2, \ldots, f_n)$ denotes the score normalized as probability for the feature subset $(f_1, f_2, \ldots, f_n)$. Then, $P(f_1|f_2, \ldots, f_n)$ is the score normalized as probability of feature $f_1$ given that features $(f_2, \ldots, f_n)$ have already been selected.

Scores converted to probabilities can be combined according to the chain rule $(P(f_1, f_2, \ldots, f_n) = P(f_1|f_2, \ldots, f_n) P(f_2, \ldots, f_n).)$ or Bayes rule $(P(f_1, f_2, \ldots, f_n) = \Sigma_i P(f_1, f_2, \ldots, f_n|C_i) P(C_i)$, where $C_i$ could be various means of scoring using different experimental data or evidence and $P(C_i)$ would be weights measuring the reliability of such data source $(\Sigma_i P(C_i) = 1)$.

Scoring a large number of feature subsets is often computationally impractical. One can attempt to estimate the score of a larger subset of features from the scores of smaller subsets of features by making independence assumptions, i.e., $P(f_1, f_2, \ldots, f_n) = P(f_1) P(f_2) \ldots P(f_n)$. Or, if there are scores for pairs of features, scores for triplets can be derived by replacing $P(f_1, f_2, f_3) = P(f_1, f_2|f_3) P(f_3) = P(f_1, f_3|f_2)P(f_2) = P(f_2, f_3|f_1)P(f_1)$ with $P(f_1, f_2, f_3) = (\frac{1}{3})(P(f_1, f_2|f_3) P(f_3) + P(f_1, f_3|f_2)P(f_2) + P(f_2, f_3|f_1)P(f_1))$. Other scores for large numbers of features can be derived from the scores of small numbers of features in a similar manner.

One of the simplest structures for representing alternative choices of features is a ranked list. The features are sorted according to their scores such that the most promising features according to that score is top ranked and the least promising features are ranked lowest. The opposite order is also possible. Scores include prediction success rate of a classifier built using a single feature; absolute value of the weights of a linear classifier; value of a correlation coefficient between the feature vector and the target feature vector consisting of (+1) and (−1) values corresponding to class lables A or B (in a two class problem). Correlation coefficients include the Pearson correlation coefficient; value of the Fisher criterion in a multi-class problem.

It is often desirable to select a subset of features that complement each other to provide best prediction accuracy. Using a ranked list of features, one can rank subsets of features. For example, using scores normalized as probabilities and making feature independence assumptions, the above-described chain rule can be applied.

Independence assumptions are often incorrect. Methods of forward features selection or backward elimination (including RFE, discussed below) allow the construction of nested subsets of complementary features $F_1 \subset F_2 \subset \ldots F_m$ using a greedy search algorithm that progressively adds or removes features. for scores normalized as probabilities, the chain rule applies. For example, assume $F_1 = \{f_a\}$ and $F_2 = \{f_a, f_b\}$. The relationship $P(F_2) = P(F_1)P(F_2|F_1) = P(f_a)P(f_a, f_b|f_a)$ is a forward selection scheme where $f_b$ can be added once $f_a$ has been selected with the probability $P(f_a, f_b|f_a)$ of making a good choice. Similarly, if it is assumed that $F_{m-1} = (f_a, f_b, \ldots, f_j)$ and $F_m = (f_a, f_b, \ldots f_j, f_k)$, then $P(F_{m-1}) = P(F_m)P(F_{m-1}|F_m) = P(f_a, f_b, \ldots f_j, f_k)P(f_a, f_b, \ldots, f_j|f_a, f_b, \ldots f_j, f_k)$. This can be read in a backward elimination scheme as: eliminate $f_k$ when the remaining subset is $\{f_a, f_b, \ldots f_j, f_k\}$, with probability $P(f_a, f_b, \ldots f_j|f_a, f_b, \ldots f_j, f_k)$ of making a good choice.

Alternatively, one can add or remove more than one feature at a time. (See detailed description of RFE below.) As an example, RFE-SVM is a backward elimination procedure that uses as the score to rank the next feature to be eliminated a quantity that approximates the difference in success rate $S(F_{m-1})-S(F_m)$. Scores are additive and probabilities multiplicative, so by using exponentiation and normalization, the score difference can be mapped to $P(F_{m-1}|F_m)=1$ because of the backward elimination procedures. Since $P(F_m)$ is proportional to $exp(S_m)$, $P(F_{m-1}|F_m)=P(F_m|F_{m-1})P(F_{m-1})/P(F_m)=exp(S_{m-1}/S_m)$. In a manner similar to that described for ranked lists of subsets of equivalent features, nested subsets can be constructed of complementary subsets of equivalent features. Clustering can be used to create "super features" (cluster centers). The nested subsets of super features define nested subsets of subsets of equivalent features, i.e., the corresponding clusters.

In an alternative method, nested subsets of complementary features can be constructed using cardinality increment of one. The first few subsets are kept, then the remaining features are aggregated to the features in the nested subset. In other words, the features in the nested subset are used as cluster centers, then clusters are formed around those centers with the remaining features. One application of such structures is the selection of alternate subsets of complementary features by replacing the cluster centers in a subset of cluster centers with one of the cluster members.

Nested subsets of complementary subsets of equivalent features may produce alternate complementary subsets of features that are sub-optimal. Trees can provide a better alternative for representing a large number of alternate nested subsets of complementary features. Each node of the tree is labeled with a feature and a feature subset score. The children of the root node represent alternate choices for the first feature. The children of the children of the root are alternate choices for the second features, etc. The path from the root node to a given node is a feature subset, the score of which is attached to that node.

The score for siblings is the score of the subset including the child feature and all its ancestors. For scores normalized to probabilities, sorting of the siblings is done according to the joint probability P(ancestors, child). Given that siblings share the same ancestors, such sibling ranking also corresponds to a ranking according to P(child|ancestors). This provides a ranking of alternate subsets of features of the same size.

Trees can be built with forward selection algorithms, backward selection algorithms, exhaustive feature subset evaluation or other search strategies. Trees are structures that generalize both ranked lists and nested subsets of features. A tree of depth one is a ranked list (of all children of the root.) A tree that has only one branch defines nested subsets of features. One can also build trees of super-features (cluster centers) and, therefore, obtain a structure that contains multiple alternative of nested subsets of subsets of equivalent features. Another variant is to build a tree using only the top features of a ranked list. Subsequently, the features eliminated can be aggregated to the nodes of the tree they most resemble.

Other graphs, particularly other kinds of directed acyclic graphs, may have some relevance to describe subsets of features. For example, Bayesian networks have been used to describe relationships between genes.

For some features, e.g., genes, one can obtain patterns from various sources. Assume that one wishes to assess the relevance of certain genes with respect to a given disease. Gene scores (or gene subsest scores) can be derived from DNA microarray gene expression coefficients for a variety of diseased and normal patients. Other scores can be obtained from protein arrays, and still other scores can be obtained by correlation of the citation of various genes with the given disease from published medical articles. In each case, a feature subset data structure can be constructed. These structures can then be combined to select feature subsets based on the combined information.

When combining information from different data sources, ranked lists are typically the easiest to combine. For a ranking of n features (or feature subsets) from two different sources, let $S_1, S_2, \ldots, S_n$ be the scores for the first source and $S'_1, S'_2, \ldots, S'_n$ be the scores for the second source. If the scores used to rank the two list are commensurate, then a new ranked list can be created using a combined score for every feature. The combination can be, for example, additive ($S_1+S'_1, S_2+S'_2, \ldots, S_n+S'_n$) or multiplicative ($S_1S'_1, S_2S'_2, \ldots, S_nS'_n$). Different types of score combinations yield different rankings. If the scores are not commensurate, they can be replaced by scores having no dimension. In this case, the rank of the features in the two lists are $S_i$, which is the rank of feature subset i in the list ranked according to $S_j$, j=1 . . . n, and $S'_i$, which is the rank of feature subset i in the list ranked according to $S'_j$, j=1 . . . n.

All of the above-proposed schemes can be trivially generalized to combinations of more than two scores.

Scores can be made commensurate by normalizing them to probability-like scores. If the scores are probability-like quantities, additive combinations might be interpreted as voting according to the confidence $P(source_i)$ that one has in the various sources of information: $P(feature\ subset_i)=P(feature\ subset_i|source_i)\ P(source_i)$.

If not all of the feature subsets scored using the data from the first source are scored using the data from the second source, they can still be combined by using the intersection of the subsets scored. Alternatively, one can complete the missing scores is each list explicitly by computing them, or approximate by using independence assumptions.

Ranked lists and nested subsets of features can be composed rather than combined. One can first rank the features according to a given score, selecting the top ranked features, then create a nested subset of features on the remaining subset. Such a combination of operations makes sense in cases where a given nested subset of features algorithm is prone to "overfit" the data, i.e., choose combinations of features that have a small prediction error on training examples, but a large prediction error on new test examples. Using a feature ranking algorithm first may reduce the risk of overfitting by eliminating those features that are poorly correlated to the target and coincidentally complement each other.

Trees and ranked lists are easily combined using methods for combining ranked lists. One uses the fact that the siblings in a tree constitute a ranked list, the score of each node being the score of all the features from the root to the given node. That ranked list can be combined with another ranked list that gives scores for the same feature subsets. A new tree is built with the combined scores and the siblings are ranked again accordingly. Lists containing missing values can be truncated or completed.

Combining trees can be done in a similar way. This amounts to combining the scores of the feature subsets found in the tree, by completing missing values if necessary, and re-ranking the siblings.

In the case where scores are probability-like, the scores used to rank the siblings $P(child=feature_i|ancestors, source_i)$ in a tree built from data source 1 can be combined with the scores used to rank the siblings $P(child=feature_i|ancestors, source_2)$ in a tree built from data source 2 as P(child=feature$_i$|ancestors)=P(child=feature$_i$|ancestors, source$_1$) P(source$_1$)+P(child=feature$_i$|ancestors, source$_2$)P(source$_2$).

There is a particular case in which the second tree is built from scores obtained by making independence assumptions, P(f$_1$, f$_2$, f$_n$)=P(f$_1$).P(f$_2$) . . . P(f$_n$). In that case, P(child=feature$_i$|ancestors, source$_2$) P(feature$_i$|source$_2$).

Other methods of combining structurese of relevant features will become apparent to those of skill in the art based on the preceding examples.

In one method of feature selection, a pre-processing operation may involve the use of expert knowledge to eliminate data that are known to complicate analysis due to the difficulty in differentiating the data from other data that is known to be useful. In the colon cancer example used above, tissue composition-related genes were automatically eliminated in the pre-processing step by searching for the phrase "smooth muscle" in the description of the gene. Other means for searching the data for indicators of the smooth muscle genes may be used.

Feature Selection by Recursive Feature Elimination.

While the illustrative examples are directed at gene expression data manipulations, any data can be used in the methods, systems and devices described herein. There are studies of gene clusters discovered by unsupervised or supervised learning techniques. Preferred methods comprise application of SVMs in determining a small subset of highly discriminant genes that can be used to build very reliable cancer classifiers. Identification of discriminant genes is beneficial in confirming recent discoveries in research or in suggesting avenues for research or treatment. Diagnostic tests that measure the abundance of a given protein in bodily fluids may be derived from the discovery of a small subset of discriminant genes.

In classification methods using SVMs, the input is a vector referred to as a "pattern" of n components referred to as "features". F is defined as the n-dimensional feature space. In the examples given, the features are gene expression coefficients and the patterns correspond to patients. While the present discussion is directed to two-class classification problems, this is not to limit the scope of the invention. The two classes are identified with the symbols (+) and (−). A training set of a number of patterns $\{x_1, x_2, \ldots x_k, \ldots x_l\}$ with known class labels $\{y_1, y_2, \ldots y_k, \ldots y_l\}, y_k \in \{-1, +1\}$, is given. The training patterns are used to build a decision function (or discriminant function) D(x), that is a scalar function of an input pattern x. New patterns are classified according to the sign of the decision function:

D(x)>0⇒x∈class (+);
D(x)<0⇒x∈class (−);
D(x)=0, decision boundary;

where ∈ means "is a member of".

Decision boundaries that are simple weighted sums of the training patterns plus a bias are referred to as "linear discriminant functions", e.g., $$D(x)=w \cdot x+b, \quad (1)$$

where w is the weight vector and b is a bias value. A data set is said to be linearly separable if a linear discriminant function can separate it without error.

Feature selection in large dimensional input spaces is performed using greedy algorithms and feature ranking. A fixed number of top ranked features may be selected for further analysis or to design a classifier. Alternatively, a threshold can be set on the ranking criterion. Only the features whose criterion exceed the threshold are retained. A preferred method uses the ranking to define nested subsets of features, $F_1 \subset F_2 \subset \ldots \subset F$, and select an optimum subset of features with a model selection criterion by varying a single parameter: the number of features.

Errorless separation can be achieved with any number of genes greater than one. Preferred methods comprise use of a smaller number of genes. Classical gene selection methods select the genes that individually best classify the training data. These methods include correlation methods and expression ratio methods. While the classical methods eliminate genes that are useless for discrimination (noise), they do not yield compact gene sets because genes are redundant. Moreover, complementary genes that individually do not separate well are missed.

A simple feature ranking can be produced by evaluating how well an individual feature contributes to the separation (e.g. cancer vs. normal). Various correlation coefficients have been proposed as ranking criteria. For example, see, T. K. Golub, et al, "Molecular classification of cancer: Class discovery and class prediction by gene expression monitoring", Science 286, 531-37 (1999). The coefficient used by Golub et al. is defined as:

$$w_i=(\mu_i(+)-\mu_i(-))/(\sigma_i(+)+\sigma_i(-)) \quad (2)$$

where $\mu_i$ and $\mu_i$ are the mean and standard deviation, respectively, of the gene expression values of a particular gene i for all the patients of class (+) or class (−), i=1, . . . n . . . . Large positive $w_i$ values indicate strong correlation with class (+) whereas large negative $w_i$ values indicate strong correlation with class (−). The method described by Golub, et al. for feature ranking is to select an equal number of genes with positive and with negative correlation coefficient. Other methods use the absolute value of $w_i$ as ranking criterion, or a related coefficient, $$(\mu_i(+)-\mu_i(-))^2/(\sigma_i(+)^2+\sigma_i(-)^2) \quad (3)$$

What characterizes feature ranking with correlation methods is the implicit orthogonality assumptions that are made. Each coefficient $w_i$ is computed with information about a single feature (gene) and does not take into account mutual information between features.

One use of feature ranking is in the design of a class predictor (or classifier) based on a pre-selected subset of genes. Each feature which is correlated (or anti-correlated) with the separation of interest is by itself such a class predictor, albeit an imperfect one. A simple method of classification comprises a method based on weighted voting: the features vote in proportion to their correlation coefficient. Such is the method used by Golub, et al. The weighted voting scheme yields a particular linear discriminant classifier:

$$D(x)=w \cdot (x-\mu), \quad (4)$$

where w is $w_i=(\mu_i(+)-\mu_i(-))/(\sigma_i(+)+\sigma_i(-))$ and $\mu=(\mu(+)+\mu(-))/2$ Another classifier or class predictor is Fisher's linear discriminant. Such a classifier is similar to that of Golub et al. where $$w=S^{-1}(\mu(+)+\mu(-)), \quad (5)$$

where S is the (n,n) within class scatter matrix defined as $$S = \sum_{x \in X(+)} (x-\mu(+))(x-\mu(+))^T + \sum_{x \in X(-)} x-\mu(-))(x-\mu(-))^T, \quad (6)$$

where μ is the mean vector over all training patterns and X(+) and X(−) are the training sets of class (+) and (−), respectively. This form of Fisher's discriminant implies that S is invertible, however, this is not the case if the number of features n is larger than the number of examples l since the rank of S is at most l. The classifiers of Equations 4 and 6 are similar if the scatter matrix is approximated by its diagonal elements. This approximation is exact when the vectors formed by the values of one feature across all training patterns are orthogonal, after subtracting the class mean. The approximation retains some validity if the features are uncorreclated, that is, if the expected value of the product of two different features is zero, after removing the class mean. Approximating S by its diagonal elements is one way of regularizing it (making it invertible). However, features usually are correlated and, therefore, the diagonal approximation is not valid.

One aspect of the present invention comprises using the feature ranking coefficients as classifier weights. Reciprocally, the weights multiplying the inputs of a given classifier can be used as feature ranking coefficients. The inputs that are weighted by the largest values have the most influence in the classification decision. Therefore, if the classifier performs well, those inputs with largest weights correspond to the most informative features, or in this instance, genes. Other methods, known as multivariate classifiers, comprise algorithms to train linear discriminant functions that provide superior feature ranking compared to correlation coefficients. Multivariate classifiers, such as the Fisher's linear discriminant (a combination of multiple univariate classifiers) and methods disclosed herein, are optimized during training to handle multiple variables or features simultaneously.

For classification problems, the ideal objective function is the expected value of the error, i.e., the error rate computed on an infinite number of examples. For training purposes, this ideal objective is replaced by a cost function J computed on training examples only. Such a cost function is usually a bound or an approximation of the ideal objective, selected for convenience and efficiency. For linear SVMs, the cost function is:

$$J=(1/2)\|w\|^2, \quad (7)$$

which is minimized, under constraints, during training. The criteria $(w_i)^2$ estimates the effect on the objective (cost) function of removing feature i.

A good feature ranking criterion is not necessarily a good criterion for ranking feature subsets. Some criteria estimate the effect on the objective function of removing one feature at a time. These criteria become suboptimal when several features are removed at one time, which is necessary to obtain a small feature subset.

Recursive Feature Elimination (RFE) methods can be used to overcome this problem. RFE methods comprise iteratively 1) training the classifier, 2) computing the ranking criterion for all features, and 3) removing the feature having the smallest ranking criterion. This iterative procedure is an example of backward feature elimination. For computational reasons, it may be more efficient to remove several features at a time at the expense of possible classification performance degradation. In such a case, the method produces a "feature subset ranking", as opposed to a "feature ranking". Feature subsets are nested, e.g., $F_1 \subset F_2 \subset \ldots \subset F$.

If features are removed one at a time, this results in a corresponding feature ranking. However, the features that are top ranked, i.e., eliminated last, are not necessarily the ones that are individually most relevant. It may be the case that the features of a subset $F_m$ are optimal in some sense only when taken in some combination. RFE has no effect on correlation methods since the ranking criterion is computed using information about a single feature.

In the present embodiment, the weights of a classifier are used to produce a feature ranking with a SVM (Support Vector Machine). The present invention contemplates methods of SVMs used for both linear and non-linear decision boundaries of arbitrary complexity, however, the example provided herein is directed to linear SVMs because of the nature of the data set under investigation. Linear SVMs are particular linear discriminant classifiers. (See Equation 1). If the training set is linearly separable, a linear SVM is a maximum margin classifier. The decision boundary (a straight line in the case of a two-dimension separation) is positioned to leave the largest possible margin on either side. One quality of SVMs is that the weights $w_i$ of the decision function D(x) are a function only of a small subset of the training examples, i.e., "support vectors". Support vectors are the examples that are closest to the decision boundary and lie on the margin. The existence of such support vectors is at the origin of the computational properties of SVM and its competitive classification performance. While SVMs base their decision function on the support vectors that are the borderline cases, other methods such as the previously-described method of Golub, et al., base the decision function on the average case.

A preferred method of the present invention comprises using a variant of the soft-margin algorithm where training comprises executing a quadratic program as described by Cortes and Vapnik in "Support vector networks", 1995, *Machine Learning*, 20:3, 273-297, which is incorporated herein by reference in its entirety. The following is provided as an example, however, different programs are contemplated by the present invention and can be determined by those skilled in the art for the particular data sets involved.

Inputs comprise training examples (vectors) $\{x_1, x_1, \ldots x_k \ldots x_l\}$ and class labels $\{y_1, y_2 \ldots y_k \ldots y_l\}$. To identify the optimal hyperplane, the following quadratic program is executed:

$$\begin{cases} \text{Minimize over } \alpha_k: \\ J = (1/2)\sum_{hk} y_h y_k \alpha_h \alpha_k (x_h \cdot x_k + \lambda \delta_{hk}) - \sum_k \alpha_k \\ \text{subject to:} \\ 0 \leq \alpha_k \leq C \text{ and } \sum_k \alpha_k y_k = 0 \end{cases} \quad (8)$$

with the resulting outputs being the parameters $\alpha_k$, where the summations run over all training patterns $x_k$ that are n dimensional feature vectors, $x_h \cdot x_k$ denotes the scalar product, $y_k$ encodes the class label as a binary value=1 or −1, $\delta_{hk}$ is the Kronecker symbol ($\delta_{hk}=1$ if h=k and 0 otherwise), and X and C are positive constants (soft margin parameters). The soft margin parameters ensure convergence even when the problem is non-linearly separable or poorly conditioned. In such cases, some support vectors may not lie on the margin. Methods include relying on λ or C, but preferred methods, and those used in the Examples below, use a small value of λ (on the order of $10^{-14}$) to ensure numerical stability. For the Examples provided herein, the solution is rather insensitive to the value of C because the training data sets are linearly separable down to only a few features. A value of C=100 is adequate, however, other methods may use other values of C.

The resulting decision function of an input vector x is:

$$D(x) = w \cdot x + b \tag{9}$$

with $$w = \sum_k \alpha_k y_k x_k \text{ and } b = \langle y_k - w \cdot x_k \rangle$$

The weight vector w is a linear combination of training patterns. Most weights $\alpha_k$ are zero. The training patterns with non-zero weights are support vectors. Those having a weight that satisfies the strict inequality $0<\alpha_k<C$ are marginal support vectors. The bias value b is an average over marginal support vectors.

The following sequence illustrates application of recursive feature elimination (RFE) to a SVM using the weight magnitude as the ranking criterion. The inputs are training examples (vectors): $X_0=[x_1, x_2, \ldots x_k \ldots x_l]^T$ and class labels $Y=[y_1, y_2 \ldots y_k \ldots y_l]^T$.

Initalize:
Subset of surviving features
s=[1, 2, ... n]
Features ranked list
r=[ ]
Repeat until s=[ ]
Restrict training examples to good feature indices
$X=X_0(:,s)$
Train the classifier
$\alpha$=SVM train(X,y)
Compute the weight vector of dimension length(s):

$$w = \sum_k \alpha_k y_k x_k$$

Compute the ranking criteria
$c_i=(w_i)^2$, for all i
Find the feature with smallest ranking criterion
f=argmin(c)
Update feature ranked list
r=[s(f),r]

Eliminate the feature with smallest ranking criterion
s=s(1:f −1, f=1:length (s))
The output comprises feature ranked list r.

The above steps can be modified to increase computing speed by generalizing the algorithm to remove more than one feature per step.

In general, RFE is computationally expensive when compared against correlation methods, where several thousands of input data points can be ranked in about one second using a Pentium® processor, and weights of the classifier trained only once with all features, such as SVMs or pseudo-inverse/mean squared error (MSE). A SVM implemented using non-optimized MatLab® code on a Pentium® processor can provide a solution in a few seconds. To increase computational speed, RFE is preferably implemented by training multiple classifiers on subsets of features of decreasing size. Training time scales linearly with the number of classifiers to be trained. The trade-off is computational time versus accuracy. Use of RFE provides better feature selection than can be obtained by using the weights of a single classifier. Better results are also obtained by eliminating one feature at a time as opposed to eliminating chunks of features. However, significant differences are seen only for a smaller subset of features such as fewer than 100. Without trading accuracy for speed, RFE can be used by removing chunks of features in the first few iterations and then, in later iterations, removing one feature at a time once the feature set reaches a few hundreds. RFE can be used when the number of features, e.g., genes, is increased to millions. In one example, at the first iteration, the number of genes were reached that was the closest power of two. At subsequent iterations, half of the remaining genes were eliminated, such that each iteration was reduced by a power of two. Nested subsets of genes were obtained that had increasing information density.

RFE consistently outperforms the naïve ranking, particularly for small feature subsets. (The naïve ranking comprises ranking the features with $(w_i)^2$, which is computationally equivalent to the first iteration of RFE.) The naïve ranking organizes features according to their individual relevance, while RFE ranking is a feature subset ranking. The nested feature subsets contain complementary features that individually are not necessarily the most relevant. An important aspect of SVM feature selection is that clean data is most preferred because outliers play an essential role. The selection of useful patterns, support vectors, and selection of useful features are connected.

In addition to the above-described linear example, SVM-RFE can be used in nonlinear cases and other kernel methods. The method of eliminating features on the basis of the smallest change in cost function can be extended to nonlinear uses and to all kernel methods in general. Computations can be made tractable by assuming no change in the value of the $\alpha$'s. Thus, the classifer need not be retrained for every candidate feature to be eliminated.

Specifically, in the case of SVMs, the cost function to be minimized (under the constraints $0 \leq \alpha_k \leq C$ and $\Sigma_k \alpha_k y_k=0$) is:

$$J=(\tfrac{1}{2})\alpha_T H\alpha - \alpha^T 1, \tag{10}$$

where H is the matrix with elements $y_h y_k K(x_h x_k)$, K is a kernel function that measures the similarity between $x_h$ and $x_k$, and 1 is an l dimensional vector of ones.

An example of such a kernel function is $$K(x_h x_k)=\exp(-\gamma\|x_h-x_k\|^2) \tag{11}$$

To compute the change in cost function caused by removing input component i, one leaves the $\alpha$'s unchanged and recomputes matrix H. This corresponds to computing $K(x_h(-i), x_k(-i))$, yielding matrix $H(-i)$, where the notation $(-i)$ means that component i has been removed. The resulting ranking coefficient is:

$$DJ(i)=(\tfrac{1}{2})\alpha^T H\alpha -(\tfrac{1}{2})\alpha^T H(-i)\alpha \tag{12}$$

The input corresponding to the smallest difference DJ(i) is then removed. The procedure is repeated to carry out Recursive Feature Elimination (RFE).

A method for predicting the optimum subset of data can comprise defining a criterion of optimality that uses information derived from training examples only. This criterion can be checked by determining whether a predicted data subset performed best on the test set.

A criterion that is often used in similar "model selection" problems is the leave-one-out success rate $V_{suc}$. In some cases, it may be of little use since differentiation between many classifiers that have zero leave-one-out error is not allowed. Such differentiation is obtained by using a criterion that combines all of the quality metrics computed by cross-validation with the leave-one-out method:

$$Q=V_{suc}+V_{acc}+V_{ext}+V_{med} \tag{13}$$

where $V_{suc}$ is the success rate, $V_{acc}$ the acceptance rate, $V_{ext}$ the extremal margin, and $V_{med}$ is the median margin.

Theoretical considerations suggest modification of this criterion to penalize large gene sets. The probability of observing large differences between the leave-one-out error and the test error increases with the size d of the data set, according to $$\epsilon(d)=\text{sqrt}(-\log(\alpha)+\log(G(d))).\text{sqrt}(p(1-p)/n) \quad (14)$$

where $(1-\alpha)$ is the confidence (typically 95%, i.e., $\alpha=0.05$), p is the "true" error rate (p<=0.01), and n is the size of the training set.

Following the guaranteed risk principle, a quantity proportional to $\epsilon(d)$ was subtracted from criterion Q to obtain a new criterion:

$$C=Q-2\epsilon(d) \quad (15)$$

The coefficient of proportionality was computed heuristically, assuming that $V_{suc}, V_{acc}, V_{ext}$ and $V_{med}$ are independent random variables with the same error bar $\epsilon(d)$ and that this error bar is commensurate to a standard deviation. In this case, variances would be additive, therefore, the error bar should be multiplied by sqrt(4).

The leave-one-out method with the classifier quality criterion can be used to estimate the optimum number of data points. The leave-one-out method comprises taking out one example of the training set. Training is then performed on the remaining examples, with the left out example being used to test the trained classifier. This procedure is iterated over all the examples. Each criteria is computed as an average over all examples. The overall classifier quality criterion is calculated according to Equation 13. The classifier is a linear classifier with hard margin.

Results of the SVM-RFE as taught herein show that at the optimum predicted by the method using training data only, the leave-one-out error is zero and the test performance is actually optimum.

According to the present invention, a number of different methods are provided for selection of features in order to train a learning machine using data that best represents the essential information to be extracted from the data set. The inventive methods provide advantages over prior art feature selection methods by taking into account the interrelatedness of the data, e.g., multi-label problems. The feature selection can be performed as a pre-processing step, prior to training the learning machine, and can be done in either input space or feature space.

Data Cleaning Data cleaning is the problem of identifying mislabeled or meaningless data points. Removal or correction of mislabeled or meaningless data can improve the performance of the classifier, and in the case of feature selection algorithms, leads to more meaningful features. In the case of removal, an automatic data cleaning operation can be performed to remove bad features. Where correction is desired, some form of intervention is required to contact the source of the data (the "data collector") to confirm that the data that was received was properly transmitted, or to prompt the provider to review and possibly repeat the test to generate replacement data.

A number of algorithms may be used to identify mislabeled patterns. In the preferred embodiment, the algorithms are of the following form: they are given as input a training set $S_l$ and the output a rank $r_i$ for l data points. The rank indicates the likelihood of being an outlier, with greater likelihood being assigned a lower rank.

Measuring the success of a data cleaning algorithm, even when there is only a single mislabeled point, is not obvious.

Taking the main rank of the (single) mislabeled points is an obvious measure, however, it can pay too much attention to a few large scores. For example, if one algorithm predicts the mislabeled points on 9 out of 10 runs with rank 1, but on the other run assigns a rank of 50 to the mislabeled point, it obtains a mean of 5.9. If another algorithm always gives a rank of 5, however, it appears that the first algorithm is more useful for detecting outliers. If one is referring to the first one or two points to the data collector for verification, then the first algorithm will find outliers whereas the second will not.

The following measurements of error are recorded over n runs: 1) number of mislabeled points with rank 1, 2 and 3 (three separate scores); 2) mean rank of the mislabeled points $$\frac{1}{n}\sum_i r_{pi},$$

where $p_i$ is the index of the mislabeled point in run i; 3) trimmed mean $$\frac{1}{n}\sum_i \min(c, r_{pi}),$$

where $p_i$ is the index of the mislabeled point in run 1. That is, one takes the mean rank of the mislabeled points, but for ranks greater that c, their contribution to the mean is decreased. This serves to concentrate the score on the first few rankings.

The test set-up used was as follows: In toy data, 100 training sets of fixed size were randomly drawn. The label of a single training example in each set was flipped to create the mislabeled point. The data cleaning algorithms were scored according to the ranking of the mislabeled example in each set, then the mean score was taken. In real datasets that are of small size, e.g., microarray data, independent training sets cannot be randomly drawn. In this case, the label of each example is flipped in turn so that one has l copies of the original training set, each having a single mislabeled point.

The following algorithms were compared: SVM-$\xi$, which records the distance from the "correct" side of the margin $\xi_i$ of each training point; SVM-$\alpha$, which records the size of the weight $\alpha_i$ of each training point; SUB-ERR, which sub-samples the data many times, each time training a SVM and recording if each test point is mislabeled by the algorithm or not; SUB-$\alpha$, which sub-samples many time and records the weight of each training point; SUB-$\xi$, which sub-samples many time and records the distance from the correct side of the margin; LOO-$\xi$, which performs leave-one-out, each time training a SVM and recording the distance from the correct side of the margin; LOO-$W^2$, which performs leave-one-out, each time training a SVM and recording the size of the margin, which is inversely proportional to $W^2$; FLIP-$W^2$, which flips the label of each example, each time training a SVM and recording the size of the margin; and GRAD-C, which assigns a variable $C_i$ for each training point and minimizes $R^2 W^2$ using the "ridge trick".

The SVM-$\xi$ algorithm assigns the ranking by the distance of each point from the correct side of the margin, with the largest ranked first according to the following:
1. choose a value of the soft margin parameter C;
2. train the classifier [w,b]=SVM($S_l$, C);
3. calculate $\xi_i=1-1-y_i(w \cdot x_i+b)$ for all i;
4. assign $r_i$=card $\{\xi_j:\xi_j \geq \xi_i\}$ for all i.

The SVM-α algorithm uses weights where, if a point is easy to classify, its weight is zero. The more unusual the point, the larger the weight. The ranking is thus given by the weight of each point, with the largest ranked first, according the steps:
1. choose a value of the soft margin parameter C;
2. train the classifier $[\alpha, b]$=SVM-DUAL($S_i$, C);
3. assign $r_i$=card $\{\alpha_j : \alpha_j \geq \alpha_i\}$ for all i.

The SUB-ERR algorithm assigns ranking according to the average number of mislabelings, with the most mislabeled ranked first according to the sequence:
1. choose a value of the soft margin parameter C, the number of sub-sample runs p and the sub-sampling size q;
2. initialize $e_i$=0 and $u_i$=0 for all i;
3. FOR i=1 TO p runs
draw a random sub-sample of the training data of size q with indexes $tr_{j=1, \ldots, q}$;
let the remainder of the data have indexes $tst_{j=1, \ldots, l-q}$;
train a classifier $[w,b]$=SVM($\{(x_j, y_j)\}_{j=tr_1, \ldots, tr_q}$, C);
assign $u_{tst_j} = u_{tst_j}+1$ for all j;
assign $$e_{tst_j} = e_{tst_j} + \frac{1}{2}\left|y_{tst_j} - \text{sign}(w \cdot x_{tst_j} + b)\right| \text{ for all } j;$$

$$r_i = \text{card}\left\{\frac{p_j}{u_j} : \frac{p_j}{u_j} \geq \frac{p_i}{u_i}\right\} \text{ for all } i.$$

4. assign

Using the SUB-α algorithm, the ranking is given by the average weight of each point, with the largest value being ranked first, using the following:
1. choose a value of the soft margin parameter C, the number of sub-sample runs p and the sub-sampling size q;
2. initialize $e_i$=0 and $u_i$=0 for all i;
3. FOR i=1 TO p runs
draw a random sub-sample of the training data of size q with indexes $tr_{j=1, \ldots, q}$;
let the remainder of the data have indexes $tst_{j=1, \ldots, l-q}$;
train a classifier $[\alpha, b]$=SVM–DUAL($\{(x_j, y_j)\}_{j=tr_1, \ldots, tr_q}$, C);
assign $u_{tst_j} = u_{tst_j}+1$ for all j;
assign $e_{tst_j} = e_{tst_j} + \alpha_j$ for all j;
4. assign $$r_i = \text{card}\left\{\frac{p_j}{u_j} : \frac{p_j}{u_j} \geq \frac{p_i}{u_i}\right\} \text{ for all } i.$$

The SUB-ξ algorithm assigns ranking by the average distance of each point from the "correct" side of the margin, with the largest distance ranking first, according to the following:
1. choose a value of the soft margin parameter C, the number of sub-sample runs p and the sub-sampling size q;
2. initialize $e_i$=0 and $u_i$=0 for all i;
3. FOR i=1 TO p runs
draw a random sub-sample of the training data of size q with indexes $tr_{j=1, \ldots, q}$;
let the remainder of the data have indexes $tst_{j=1, \ldots, l-q}$;
train a classifier $[w, b]$=SVM($\{(x_j, y_j)\}_{j=tr_1, \ldots, tr_q}$, C);
assign $u_{tst_j} = u_{tst_j}+1$ for all j;
assign $e_{tst_j} = e_{tst_j} + 1 - y_{tst_j}(w \cdot x_{tst_j}+b)$ for all j;

4. assign $$r_i = \text{card}\left\{\frac{p_j}{u_j} : \frac{p_j}{u_j} \geq \frac{p_i}{u_i}\right\} \text{ for all } i.$$

The LOO-ξ algorithm assigns rank by the distance of each left out point from the "correct" side of the margin, with the largest ranked first according to the sequence:
1. choose a value of the soft margin parameter C;
2. FOR i=1 TO l
train the classifier $[w,b]$=SVM($S_i\setminus\{(x_i, y_i)\}$, C);
assign $e_i$=1-$y_i$($w \cdot x_i$+b);
4. assign $r_i$=card $\{e_j : e_j \geq e_i\}$ for all i.

The LOO-$W^2$ algorithm ranks according to the size of $W^2$ when leaving out each point, with the largest ranked first according to the steps:
1. choose a value of the soft margin parameter C;
2. FOR i=1 TO l
train the classifier $[\alpha, b]$=SVM–DUAL($S_i\setminus\{(x_i, y_i)\}$, C);
assign $e_i = W^2(\alpha)$;
4. assign $r_i$=card $\{e_j : e_j \leq e_i\}$ for all i.

The FLIP-$W^2$ algorithm ranks according to the size of $W^2$ when flipping each point, with the largest ranked first, following the sequence:
1. choose a value of the soft margin parameter C;
2. FOR i=1 TO l
train the classifier $[\alpha, b]$=SVM–DUAL($\{S_i\setminus\{(x_i, y_i)\}\}\cup\{(x_i, y_i)\}$, C);
assign $e_i = W^2(\alpha)$;
4. assign $r_i$=card $\{e_j : e_j\}$ for all i.

There are three other variants of the "FLIP" algorithm: FLIP-SPAN uses the span [2] as the quality measure; FLIP-DIST uses the change in distance from the margin of the flipped point. FLIP-VALID uses a validation set instead, summing the errors using a sigmoid on the distance from the margin of type $1/(1+\exp(3\times))$.

The GRAD-C algorithm minimizes $$\sup_\alpha R^2(C) W^2(\alpha, C)$$

where $W^2(\alpha) = \sum_i \alpha_i - \frac{1}{2}\sum_{i,j} \alpha_i \alpha_j y_i y_j \left(x_i \cdot x_j + \frac{1}{C_i}\delta_{ij}\right)$ subject to $0 \leq \alpha_i, \sum_i \alpha_i y_i = 0$ and $R(C) = \frac{1}{l}\sum_i \left(x_i^2 + \frac{1}{C_i}\right) - \frac{1}{l^2}\sum_{i,j}\left[(x_i \cdot x_j) + \frac{1}{C_i}\delta_{ij}\right]$ which can be solved by gradient descent. One then assigns $r_i$=card$\{C_j : C_j \leq C_i\}$ for all i.

Data cleaning algorithms can be improved by use in conjunction with feature selection techniques. One scheme is to implement with feature selection algorithm directly into the classifiers. A second is to consider different feature selection subset sizes and consider the scores across all the subset sizes.

The problem used to compare the various data cleaning algorithms consists of two Gaussian distributions in d=100 dimensions with variance 1.5/sqrt(d), one for each class label, drawing 30 training points randomly for each class. One hundred of the datasets were generated with the thirtieth data point flipped. The problem is to detect that this thirtieth data point is mislabeled. The various algorithms were compared in both hard margin and soft margin settings. The results are provided in Table 1, where the letters after the algorithm identifier imply the following: C is the value of the soft margin chosen using a validation set. 2C means two time this value (as sub-sampling involves a smaller training set). No C means a hard margin algorithm. In the sub-sampling algorithms, "300" after the name indicates the number of sub-samples used.

TABLE 1

| ALGO-RITHM | mean | rank 1 | rank ≦2 | rank ≦3 | mean ≦10 | mean ≦5 |
|---|---|---|---|---|---|---|
| SVM-α | 6.69 | 31 | 43 | 53 | 4.49 | 3.13 |
| SVM-ξ C | 4.64 | 36 | 53 | 68 | 3.68 | 2.72 |
| SUB-ERR 300 2C | 4.93 | 39 | 57 | 64 | 3.76 | 2.69 |
| SUB-ERR 300 | 5.03 | 39 | 58 | 63 | 3.77 | 2.69 |
| LOO-ξ | 6.28 | 35 | 53 | 60 | 4.18 | 2.86 |
| LOO-ξ C | 4.76 | 37 | 53 | 65 | 3.73 | 2.75 |
| FLIP-DIST C | 4.74 | 36 | 53 | 63 | 3.75 | 2.76 |
| FLIP-VALID C | 4.39 | 38 | 58 | 72 | 3.38 | 2.56 |
| GRAD-C | 4.89 | 38 | 49 | 63 | 3.86 | 2.81 |

According to the results shown in Table 1, SVM-α is not one of the better algorithms to use. SVM-ξ is simple and obvious but is, nonetheless, a reasonable algorithm. It is important to select a good value for C. Sub-sampling is generally very good is the number of samples is large enough, with the error rate decreasing with an increasing number of samples. Even sub-sampling is sensitive to the choice of C. However, sub-sampling still performs well as a data cleaning algorithm in the soft margin case and appears to be the best algorithm for this purpose.

The LOO algorithm performed fairly well, but not as well as sub-sampling. The flipping algorithms were not as good as expected, however, FLIP-DIST performed well. FLIP-VALID actually provides the best result, however, it uses extra information in the validation set. Perhaps using a validation set can be approximated by using sub-sampling, but this slows down the algorithm. GRAD-C provided good results, possibly due to the fact that the classifier found good values of C as part of the algorithm.

Information Retrieval According to the present invention, the relevance of the output of the data analysis, e.g., the identity of the genes identified as good predictors, is checked by comparison with documents retrieved using a different module. In the exemplary embodiment for application to bioinformatics, and particularly to analysis of gene expression data, the module for obtaining information from published literature is identified as the Gene Search Assistant™, or "GSA". The GSA is an online tool to assist in the analysis and verification of gene-disease-organ relationships which is driven by an in-house database, or "knowledge base", containing dynamically evolving analyst data and static "library" data on specific genes, diseases and organs. The analyst data includes references to online information sources, summaries and assessments of the referenced online sources, and the analysts' evolving determinations regarding specific gene-disease-organ triplets. For purpose of this description, such determinations are referred to as "Findings", which are described below. An analyst creates and modifies a finding using an interactive Web-based interface. A finding is composed of several fields including a bibiographic reference to online information. The referenced online information may be a web-based article, paper, bibliographic entry, database record, etc. An analyst creates and enters a bibiographic reference into the knowledge base using an interactive Web-based interface. A bibiographic reference is composed of several fields that are described in detail below.

For purposes of the following description, a "database server" is a program that stores and retrieves information on a resident database in response to commands and requests from users. A "Web server" is defined as a program that displays or "serves" web pages in response to requests by web browsers (e.g., Netscape, Internet Explorer) and other web "clients".

The following description of a Finding is the logical construct that a user sees when interacting with the application interface. This differs from the actual database design used to implement this construct. With this distinction in mind, a Finding, which has a unique identifier for each Finding, references the following information:

1. Gene Accession Number(s) (GANs): Identifier(s) associated with the gene under investigation. A Finding may optionally contain an additional field that will hold GANs of related but not identical genes.

2. Gene description: The gene description is not associated with any analyst, but is modifiable by any analyst. If the description is changed, then the resulting change will be seen by all analysts. In the full featured version, a description will be "owned" by" (associated with) either an analyst or the library, and only the owner of the description will be able to modify it. Each analyst will by default see only his or her description.

3. Gene keywords: In the demo, gene keywords are not associated with any analyst, but are modifiable by any analyst. If the keyword list is changed by an analyst, then the resulting change is seen by all analysts. In the future full-featured version, a keyword list will be "owned" by" (associated with) either an analyst or the library, and only the owner of a keyword list will be able to modify it. Each analyst will by default see only his or her keyword list.

4. Disease name: The name of the disease associated with the Finding. A disease may have more than one name associated with it.

5. Disease description: Same comment as for gene description.

6. Disease keywords: Same comment as for gene keywords.

7. Organ name: Same comment as for disease name.

8. Organ description: Same comment as for gene and disease description.

9. Organ keywords: Same comment as for gene and disease keywords.

10. Analyst's summary: The analysts evolving summary of the Finding.

11. Date/Time created: Date the Finding was initially created.

12. Date/Time last updated: Date the Finding was last updated.

The bibliographic reference is a record that references an online document which the analyst believes is germane to a Finding. The reference contains multiple fields that display the location of the document, the analyst's evaluation of the document, and the online search-path which led the analyst to the document. A bibliographic reference contains the following fields created from data entered by the analyst:

1. BibRef ID: Unique ID associated with the bibliographic reference.
2. Resource: The URL (Web address) of the information resource that was used to search for this bibref (example: http://www.yahoo.com).
3. Query: The search string used to search the above information resource. 4. Doc URL: The URL of the document that is being referenced.
5. Local Copy: A local copy of the document is saved in an archive directory when a bibliographic reference is created.
6. Pub Date: The real or estimated publication date of the document.
7. Reliability: The reliability of the document as estimated by the analyst.
8. Relevance: The relevance of the document as estimated by the analyst.
9. Novelty: The novelty of the document as estimated by the analyst.
10. Finding ID: The identifier of the Finding that was active when the bibliographic reference was created.
11. GAN(s): The gene accession number(s) of the gene referenced by the associated Finding.
12. Gene: A unique identifier associated with the gene referenced by the associated Finding.
13. Disease: The disease referenced by the associated Finding.
14. Organ: The organ referenced by the associated Finding.
15. Analyst: The analyst who created the bibliographic reference and the associated Finding.
16. Summary: The analyst's summary of this bibliographic reference.

In the preferred embodiment, the Gene Search Assistant is designed to provide controlled access to the knowledge base. Access is controlled via a list of analysts with passwords and login names.

The Gene Search Assistant uses a "session" paradigm to track analyst activity. When an analyst logs in to the GSA, that analyst is assigned a unique and automatically generated session number that is terminated upon the analyst logging out of the application. A session keeps track of the analyst's login and logout time. The session information is stored in the database and tracked via a "cookie" written into the analyst's browser cookie file. This cookie also contains the analyst's ID number and the ID of the current Finding.

Figure 9:
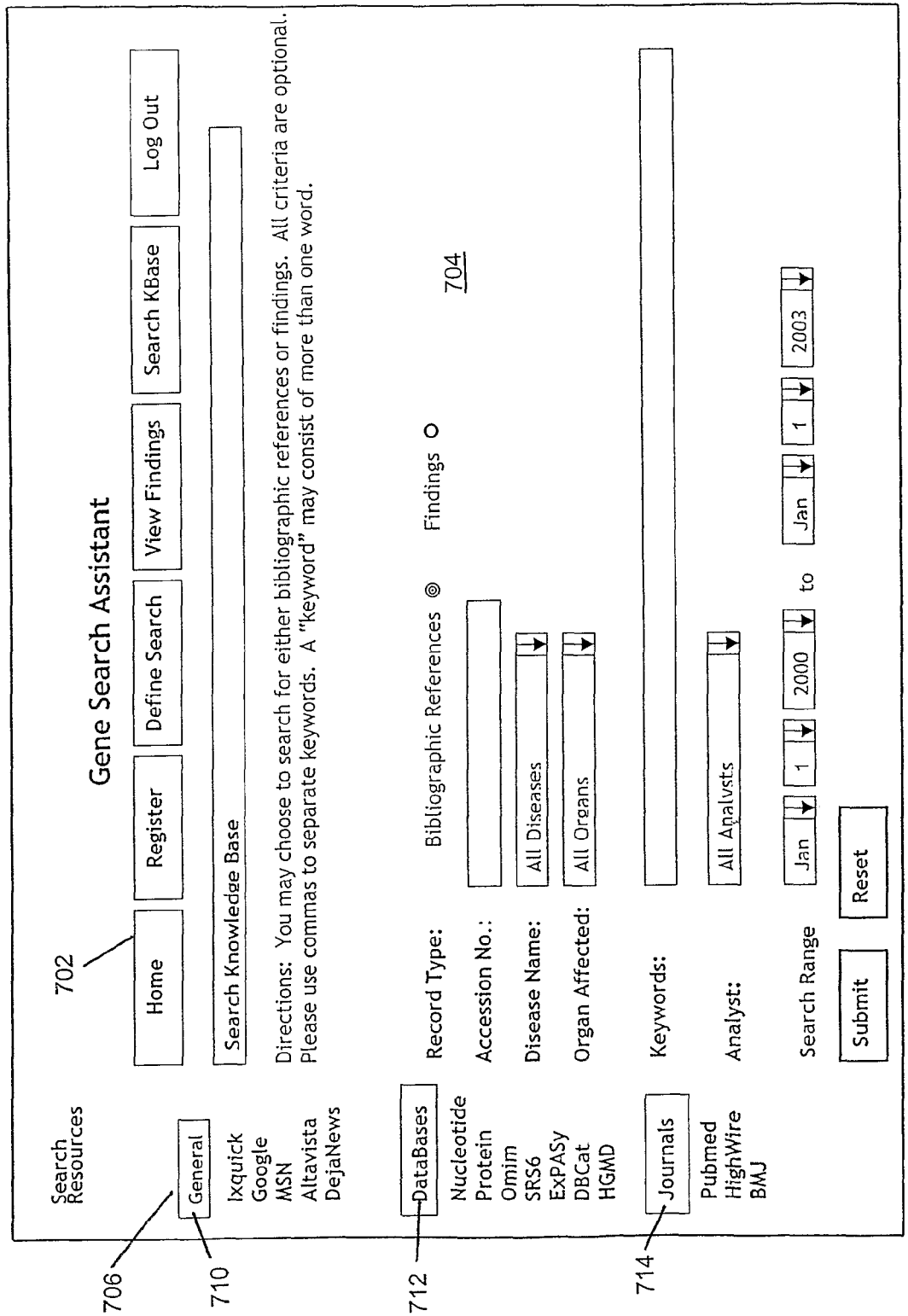
FIG. 9 is an exemplary screen shot of an interface for the Gene Search Assistant application for bioinformatics for use in searching published information.

The Gene Search Assistant is displayed on a single web page that is broken into three separate areas called "frames". Referring to FIG. 9 as an example, the top frame 702 displays links to the different functional sections of the Gene Search Assistant. The central frame 704 displays the currently selected functional section. The left frame 706, called the "navigation bar", displays links to resources on the Web external to the site on which the GSA is operating.

The top frame 702 contains links to the primary functional sections of the GSA. When a user selects a link, the chosen section is displayed in the central frame. The primary functional sections are:
1. Home: An introductory page, which also contains a login screen.
2. Register: Registration page for analysts.
3. Define Search: Allows analysts to specify the gene-disease-organ triplet which will be the subject of the current Finding.
4. View Findings: Displays an analyst's current finding, and all bibliographic references associated with that finding in a top and bottom frame.
5. Search Kbase: Contains a suite of options for searching the knowledge base. The database may be searched for Findings and bibliographic references.
6. Log Out: logout page—Allows the analyst to logout, then displays the login and logout times for the session.

When the user clicks on a link to a resource listed in the navigation bar 706, a separate web page is launched which retrieves and displays the referenced resource. The resources displayed in the navigation bar 706 are currently divided into three categories:

1. General Search Engines and Resources 710:
    Ixquick: a "meta" search engine that retrieves, combines and organizes data retrieved through a comprehensive set of on-line search engines
    Google: another meta search engine—uses a different link-based ranking strategy.
    MSN Search: Microsoft Network's meta search engine
    Altavista: A powerful general search engine
    Goto: A powerful general search engine with a different search strategy than Altavista
    Dejanews: A search engine that retrieves articles posted to Usenet news groups
    Note that although Altavista and Goto are among those search engines used by Ixquick, Google, and MSN Search to generate search results, all search engines use different ranking strategies for distinguishing relevant hits. The preceding list is not intended to be exhaustive, and other search engines are or may become available that are suitable for the purposes of the Gene Search Assistant or similar literature search module.

2. Online Genetic and Proteomic Database Resources 712:
    Entrez Nucleotide Database: A searchable collection of nucleotide entries from GenBank.
    Entrez Protein Database: The protein entries in the Entrez search and retrieval system have been compiled from a variety of sources, including SwissProt, PIR, PRF, PDB, and translations from annotated coding regions in GenBank and RefSeq.
    Omim (Online Mendelian Inheritance in Man): This database is a catalog of human genes and genetic disorders authored and edited by Dr. Victor A. McKusick and his colleagues at Johns Hopkins and elsewhere, and developed for the World Wide Web by NCBI, the National Center for Biotechnology Information.
    SRS6: SRS is a program developed at the European Bioinformatics Institute for the indexing and cross-referencing of databases of textual information. It provides unified access to molecular biology databases, integration of analysis tools and advanced parsing tools for disseminating and reformatting information stored in ASCII text.
    ExPASy: The ExPASy (Expert Protein Analysis System) proteomics server of the Swiss Institute of Bioinformatics (SIB), dedicated to the analysis of protein sequences and structures as well as 2-D PAGE.
    DBCat: The public catalog of databases.

3. Online Journals 714
    Entrez Pubmed: The National Institute of Health's online portal to Medline, PreMedline, and other related databases of journal articles and abstracts.
    HighWire: Stanford's search engine for searching across a wide cross section of peer-reviewed online journal sites.
    BMJ: medical journal search engine at the British Medical Journal similar to HighWire.

Figure 10:
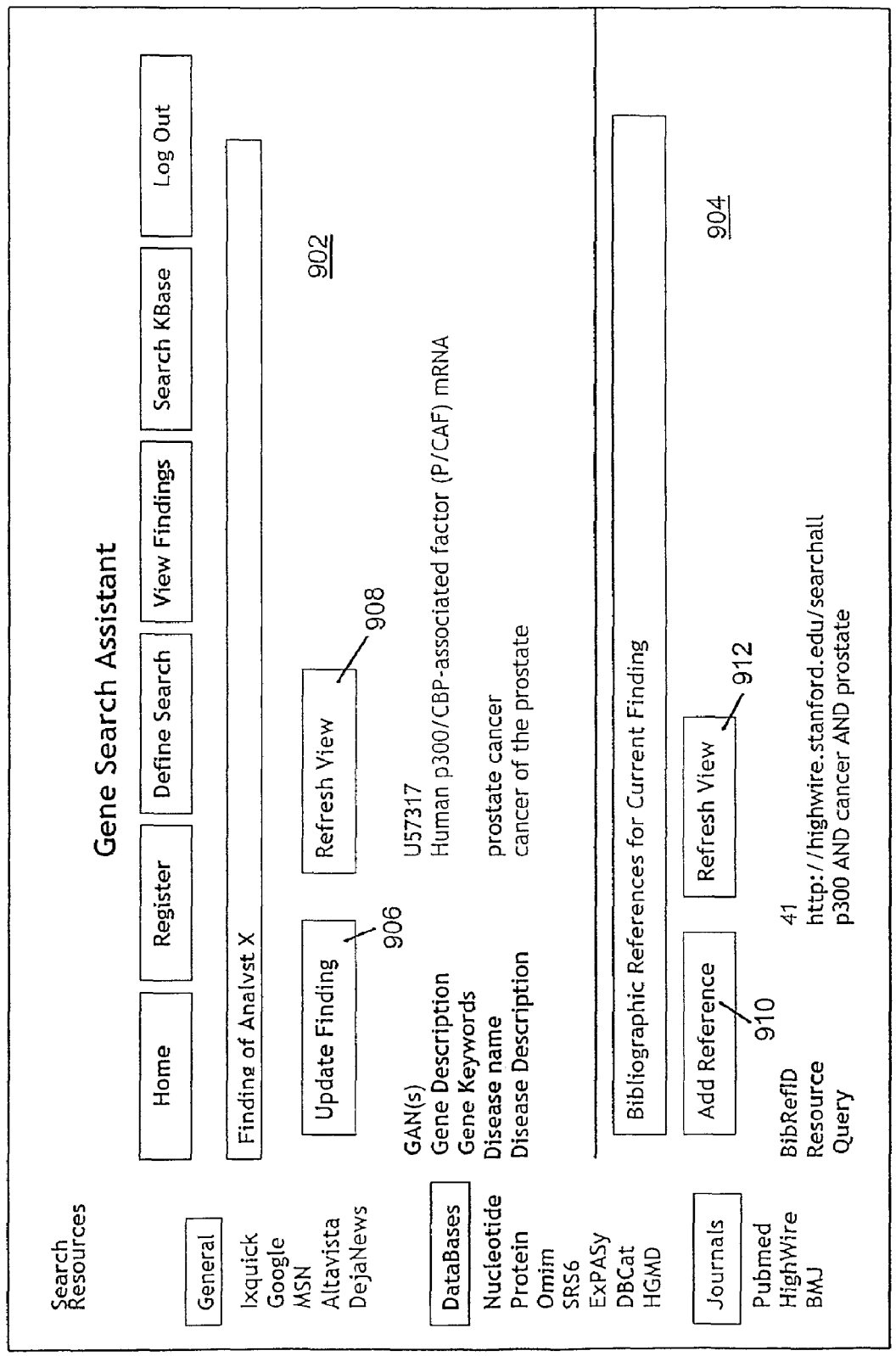
FIG. 10 is an exemplary screen shot of an interface for the Gene Search Assistant application for bioinformatics for displaying results of a search.

The central frame 704 displays the current functional section selected by the user/analyst. The home/introductory page is initially displayed by default. Following is a description of each functional section:

1. Home/Introduction: The introductory page, which appears by default when the application is entered. This page contains a description of the application, and a login form.
2. Register: Analysts who are pre-listed in a drop-menu on this page may register to use the application with a chosen login name. A random password will be automatically generated and mailed to the analyst's email address.
3. Define Search: Allows analysts to specify the gene-disease-organ triplet which will be the subject of the current Finding. If a finding by the analyst regarding the specified triplet already exists, it will be displayed along with all associated bibliographic references. If a finding corresponding to the specified triplet does not exist, one will be created.
4. View Findings: Referring to FIG. 10, the central frame is divided into two frames, a top frame 902 in which information about the current Finding is displayed, and a bottom frame 904 within which information about all bibliographic references created for that finding is displayed.
    a.) Top Frame 902: Within the top "Finding" frame, button 906 is provided which, when pressed, displays a form which the analyst can use to modify the current Finding. A second button 908 within this frame refreshes the view. After modifying the Finding, if the analyst presses second button 908, the modified Finding will be displayed in the top frame 902.
    b.) Bottom Frame 904: Within the bottom "BibRefs" frame, is button 910 which, when pressed, displays a form which the analyst can use to create a new BibRef. This new BibRef will be associated with the current Finding. A second button 912 within this frame refreshes the view. After entering a BibRef, if the analyst presses this second button, the new BibRef will be displayed in the bottom frame 904, along with all other BibRefs associated with the current Finding.
5. View Kbase: This section contains a suite of options for searching the knowledge base. The analyst can search the knowledge base for either Bibliographic References or Finding by gene, disease, organ, keywords, analyst, or date. See FIG. 9.
    The knowledge base may be searched for Findings or Bibrefs. The resulting records are displayed in the main viewing area of the browser. If an analyst searches for findings, a listing of finding summaries is displayed, each summary containing a link which when pressed displays the full finding.
6. Log Out: This section contains a logout button which allows the analyst to end the current session. Upon logout, an information screen appears displaying the login and logout time of the terminated session.

The interactive functionality of the Gene Search Assistant is provided by a web server, a database server, and CGI scripts (Common Gateway Interface programs) which allow interaction between the web pages displayed on the analyst's web browser, and the web and database servers. In a test embodiment of the Gene Search Assistant, the web server that was used was Apache, and the database server: MySQL. Both servers are open code freeware when run off in a UNIX environment. The CGI scripts for the demo were written in Perl5, a programming/scripting language.

Visualization The system of the present invention provides aids for visualization of both input and output data. In an exemplary embodiment, scores and coefficients, e.g., values of gene expression coefficients, can be visualized by associating a color map to the score values. Ranked lists of features can be visualized by printing the feature identifiers in the order of the ranked list. The identifiers can then be colored according to the scores, where each color is associated with a value according to the color map or key. Ranked lists of subsets of features can be represented in the same way, with the features identifiers being replaced by the identifiers of all features of the subset.

Ranked lists of features can also be visualized as a matrix of colored coefficients. The columns of the matrix represent all of the values a given feature takes across all patterns. The columns are ordered according to the feature ranking. The rows of the matrix may be ordered, for example, to group the examples of a same class together. A matrix can be transposed. One can also represent ranked lists of feature subsets, particularly equivalent features, in this way.

Nested subsets of features with cardinality increments of one can be visualized by printing the feature identifiers in the order that they are added to increase the cardinality of the feature subsets. The identifiers, or their background, can then be optionally colored according to the score of the subset containing all the features from the beginning of the list to that feature. For example, define an eight color map of colors 1-8, shown in FIG. 11a, where the different fill patterns indicate different colors. Assume that five features $\{f_1, f_2, f_3, f_4, f_5\}$ form nested subsets $\{f_1\} \subset \{f_1, f_4\} \subset \{f_1, f_4, f_3\} \subset \{f_1, f_4, f_3, f_2\} \subset \{f_1, f_4, f_3, f_2, f_5\}$ with scores (1, 2, 4, 5, 8). Using an elimination order, the nested subsets can be represented by the combination of colors shown in FIG. 11b, where feature $f_1$, a singleton, is indicated by a box filled with color 1 (illustrated as low density dots) to indicate the lowest score, and feature $f_5$ is filled indicated by a box filled with color 8 (illustrated as grid lines) to indicate the highest score.

Figure 11A:
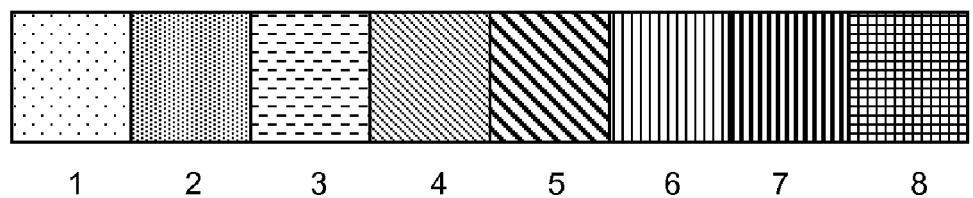
FIG. 11a is a color map for visualizing gene ranking results.
Figure 11B:
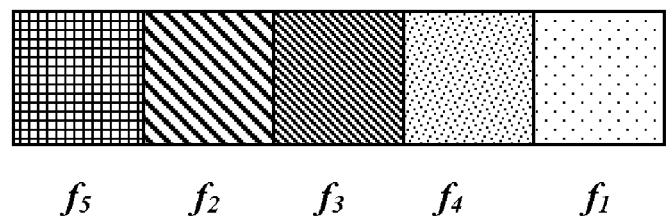
FIG. 11b is a display of a nested subsets of features using the color map of FIG. 11a to assist in visualization of the ranking.
Figure 12:
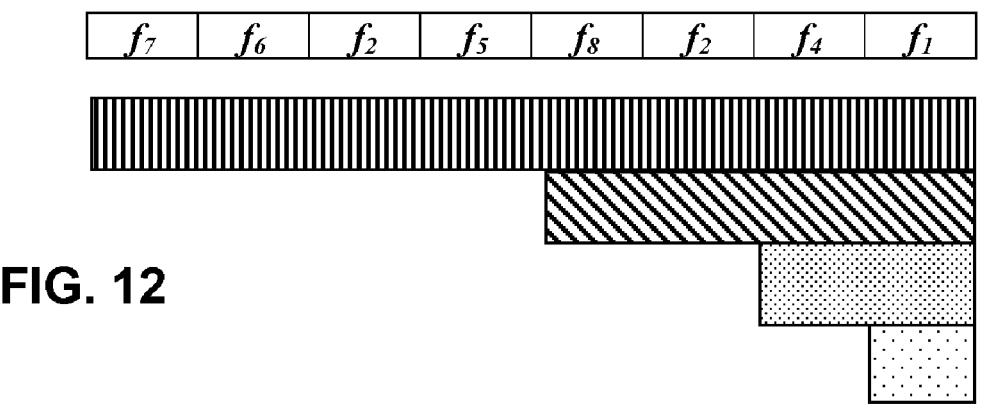
FIG. 12 is bar diagram showing a nested subset of features for visualizing gene ranking results.

Nested subsets of features with cardinality increments greater than or equal to one can be visualized as a list for which each feature belonging to a larger subset appears after other features belonging to smaller subsets. (Note that there is no unique solution; alphabetical order can be used to choose among equivalent solutions.) The subsets can be identified by bars, optionally colored according to the subset score. For example, assume eight features form nested subsets: $\{f_1\} \subset \{f_1, f_4\} \subset \{f_1, f_4, f_3, f_8\} \subset \{f_1, f_4, f_3, f_8, f_5, f_2, f_6, f_7\}$ with scores (1, 2, 4, 7). Using an elimination order, the nested subsets can be represented as shown in FIG. 12. The color map of FIG. 11a is applied to the bars. As in the previous example, $f_1$ represents the singleton at the right-most position on the diagram.

This type of visualization is easily generalized to nested subsets of subsets of equivalent features. The feature labels are replaced by the labels of the subset of equivalent features of that of the cluster center.

In a similar manner described for ranked lists, nested subsets of features can also be represented as matrices of coefficients. The order of the columns that represent all of the coefficients of a given feature follows the addition (or elimination) order of the features in the nested subsets.

Figure 13:
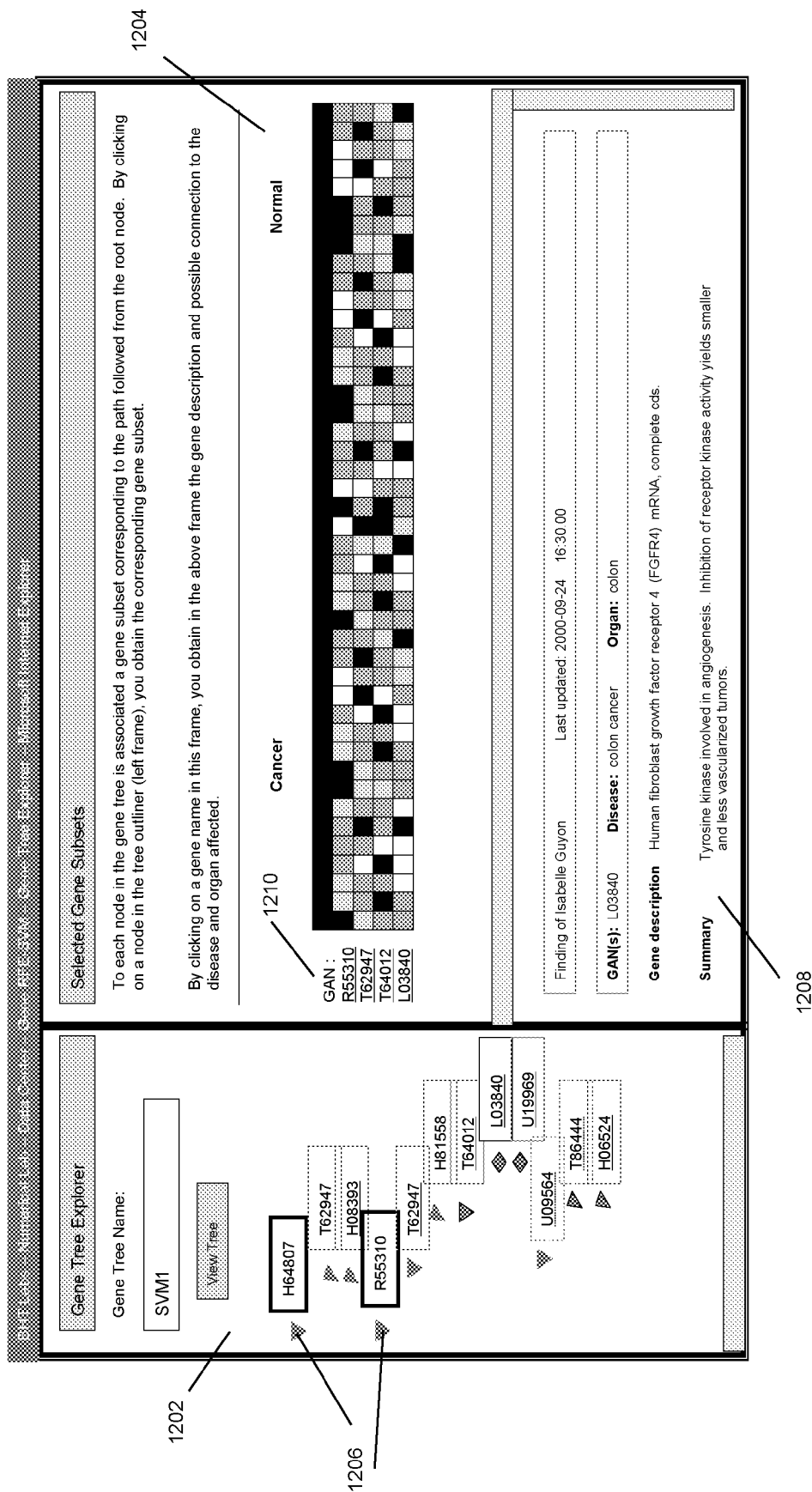
FIG. 13 illustrates an exemplary screen shot of an interface generated by the "Gene Tree Explorer" program implemented according to the present invention for analysis of gene expression data.
Figure 14:
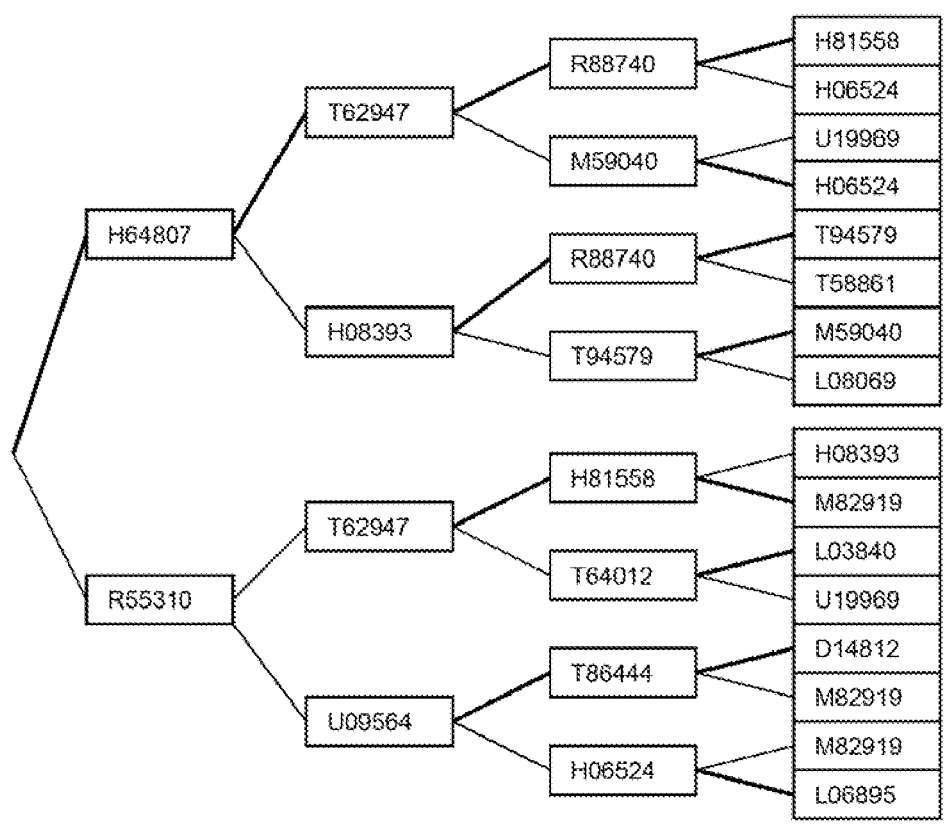
FIG. 14 is an exemplary gene observation graph, or "gene tree".

Trees can be visualized by various tree visualization software. FIG. 13 illustrates a screen shot of an interface generated by the "Gene Tree Explorer" program implemented according to the present invention. The tree (which may also be referred to as a "gene observation graph") that is represented is shown in FIG. 14. While genes are represented in this example, other types of features can be similarly represented. The nodes of the trees are marked with their feature identifier, in this case, the Gene Accession Number (GAN) 1210, and shaded, or preferably colored, according to the score of the feature subset, which was obtained by walking from the root node to that node. The left frame 1202 of the interface screen provides a link for exploring the tree by expanding the branches as needed, showing that node and all the ancestor nodes. To access the expansion for a given node, the user clicks one of the arrows 1206 next to the node, which then displays the corresponding subset in the upper right frame 1204 of the interface screen. In the upper right frame, clicking on a GAN 1210 results in retrieving additional information about that gene which was obtained from literature searches or other data sources. The retrieved information is then displayed in the bottom right frame 1208 of the interface screen.

FIG. 14 illustrates the gene tree (observation graph) corresponding to the screen information in FIG. 11. This tree was generated from DNA microarray data of colon cancer and normal patients. Several runs using the RFE-SVM algorithm were used to generate alternative nested subsets of genes. The nodes are labeled with GANs. A path from the root node to a given node in the tree at depth D defines a subset of D genes. In this case, D=4. The quality of every subset of genes can be assessed, for example, by the success rate of a classifier trained with these genes. The shading (color) of the last node of a given path indicates the quality of the subset. In the present example, a scale of 64 shades, or colors, was used to map the leave-one-out success rate.

There are several possible ways to use the observation graph. For example, consider a diagnostic test design based on the dosage of a maximum of four proteins. The statistical analysis does not take into account which protein may be easier to dose as compared to another protein. The preferred "unconstrained" path in the tree is indcated by the bold edges (darker connecting lines) in the tree, from the root node to the leaf node. This path corresponds to running plain RFE-SVM. For example, imagine that by examining the first node (H64807), it is found that this gene corresponds to a protein that is impractical to dose. One can resort to the alternative protein (R55310) and then follow the remaining unconstrained path indicated by the bold edges, or choose again the following gene according to given constraints.

In this example, a binary tree of depth 4 is construed. This means that for every gene selection, only two alternatives are presented, and that up to four genes can be selected. Wider trees (with more children at every node) permit selection from a wider variety of genes. Deeper tree provide for selection of a larger number of genes.

In the exemplary application to bioinformatics, and referring to FIG. 7, assume that the tree illustrated in FIG. 14 was generated from microarray data input into the data analysis engine 504 of the first module 500 referred to as the "Gene Discovery Lab". A second module 550, referred to as the "Gene Knowledge Finder", is used to search and processed input information comprising data extracted from biomedical literature, generating a separate tree, i.e., a "knowledge graph", identifying, e.g., a plurality of genes associated with the disease of interest. The knowledge graph incorporates present human knowledge about the genes, derived proteins, etc. A simple graph could be a set fo weights corresponding to how easily proteins can be measured in serum. The two trees are integrated into a global combined graph, also referred to as a "product graph", using data analysis engine 520. This global combined graph provides multiple alternative candidate subsets of genes with a score attached to them, providing a tool to attach a combined cost to every gene subset considered. The cost combines the subset quality (from the statistical analysis) and how promising the subset is from the knowledge graph information. The score reflects how predictive the genes are from a statistical perspective and how interesting they are from a biological perspective, providing valuable information for purposes of drug design.

This graph can be explored through a Web browser, with the knowledge base being built interactively while exploring the graph. A subset of genes that is optimum, at least in some sense, is returned to the user (customer) over the Internet link. Alternatively, the customer can be provided with the software browser and the gene graph for his/her own exploration. The graph may also be made available for exploration on a Web site.

The graph construction is implemented using MatLab® (The MathWorks, Inc., Natick, Mass.) using the following algorithm:

```
for i=2:node_num
   if (parent_of {i}= = 1) % root node
   forced in set = [ ];
   else
   forced in set = gene id (ancestor_of{i});
   force in set = forced inset (2: length (force_in_set)) %
      eliminate root node
   end
   forced_out_set = gene id ([older sibling of {[ancestor of {i} i]}]);
   if (−isempty (older_sibling of {i})) I i = = 2); % otherwise,
no need to do anything
   IGS = rfe ('omar', Xtrain, Ytrain, IG, forced_in_set, force_
out_set, div_2, dbg logfile);
   % Get indices of first descendents desc=[i
   first descendents of (i)];
   % Fill in corresponding gene numbers
   lg = length (desc)
   gn = length (IGS); gene_id (desc)=IGS (gn: −
   1: gn−lg + 1; end
   end end
```

The data mining platform of the present invention is capable of combining analysis and pre-existing knowledge from a number of different data sources. While the above-disclosed embodiment describes the platform in terms of having two distinct modules, any number of modules may be provided for handling as many types of data as are relevant to the desired analysis. Furthermore, although the disclosed embodiment relates to analysis of gene expression data and compares the results of that data analysis with information obtained from the literature search and evaluation, other disciplines will also benefit from the ability to combine heterogeneous data.

It should be understood, of course, that the foregoing relates only to preferred embodiments of the present invention and that numerous modifications or alterations may be made therein without departing from the spirit and the scope of the invention as set forth in the appended claims. Such alternate embodiments are considered to be encompassed within the spirit and scope of the present invention. Accordingly, the scope of the present invention is described by the appended claims and is supported by the foregoing description.

What is claimed is:

1. A data mining platform for generating an output comprising knowledge from analysis of a plurality of biological data sets, wherein the data sets include heterogeneous data types or the data sets come from heterogeneous data sources, the platform comprising:

a computer system programmed to implement a plurality of modules stored within a system memory, each module configured for processing one data type of the plurality of heterogeneous data types, each module comprising an input data source, a data analysis engine, a data output and a web server connection for each of the input data source, the data analysis engine and the data output, wherein the computer system comprises at least one processor for executing as part of the data analysis engine of each module one or more support vector machines for generating a plurality of classes of data and at least one margin between classes;

a web server connected to the web server connection of each module for communicating with each of the input data source, the data analysis engine and the data output of the corresponding module and for providing means for monitoring one or more of the input data source, the data analysis engine, and the data output;

a combined data analysis engine in communication with the web server for combining the data output from the plurality of modules to generate a single output representing results obtained from analyzing the plurality of heterogeneous data types; and a graphical user interface for receiving the results and generating at a printer or display device a report of organized results;

wherein the at least one processor executes multiple iterations of a feature subset ranking algorithm on a plurality of data sets comprising one or more of sub-samples of the same data set, multiple data sets of heterogeneous data types, and heterogeneous data sources, to produce ranked lists of feature subsets;

wherein the heterogeneous data types comprise one or more data types selected from the group consisting of gene expression data, 2-D gel data, mass spectrometry data, antibody screening data, clinical observations, clinical history, physical and chemical measurements, genomic determinations, proteomic determinations, drug levels, hormonal and immunological tests, neurochemical or neurophysical measurements, mineral and vitamin level determinations, and genetic and familial histories, and wherein the heterogeneous data sources comprises one or more data sources selected from the group consisting of sensor instruments for collection of genomic data, sensor instruments for collection of proteomic data, sensor instruments for collection of physical and chemical measurements, clinical record databases, general internet search engines, on-line genetic databases, on-line proteomic databases, and on-line journals; and wherein the ranked lists of feature subsets comprise lists of genes or proteins.

2. The data mining platform of claim 1, wherein the at least one processor further executes at least one pre-processing algorithm for pre-processing the input data for each module.

3. The data mining platform of claim 1, wherein the feature subset ranking algorithm comprises recursive feature elimination.

4. The data mining platform of claim 1, wherein the at least one processor generates an observation tree for visually displaying the ranked list of genes or proteins.

5. The data mining platform of claim 1, wherein the at least one processor validates an analysis obtained with one data type with the analysis obtained with another data type.

6. The data mining platform of claim 4, wherein the observation tree comprises a plurality of nodes, wherein each node of the tree is labeled with a gene or protein and a corresponding feature subset score.

7. The data mining platform of claim 6 wherein the plurality of nodes comprises root nodes and child nodes, wherein the genes or proteins corresponding to the child nodes represent alternate choices for the genes or proteins corresponding to the root nodes.

8. The data mining platform of claim 7 wherein the plurality of nodes further comprises grandchild nodes, wherein the genes or proteins corresponding to the grandchild nodes represent alternate choices for the genes or proteins corresponding to the root nodes and the child nodes.

9. The data mining platform of claim 7, wherein the alternate choices for genes or proteins are selected based upon expert knowledge.

10. The data mining platform of claim 7, wherein the alternate choices for genes or proteins are selected based upon information obtained from a different data source.

11. The data mining platform of claim 7, wherein the alternate choices for genes or proteins are selected based upon ease of detection in a biological sample.

12. A computer program product embodied on a computer readable medium for discovering knowledge from analysis of a plurality of biological data sets, wherein the data sets include heterogeneous data types of the data sets come from heterogeneous data sources, the computer program product comprising instructions for executing support vector machine classifiers and further for causing a computer processor to:

receive data from the plurality of biological data sets and;

(a) implement a plurality of modules stored within a system memory, each module configured for processing one data type of the plurality of heterogeneous data types, each module comprising an input data source, a data analysis engine, a data output and a web server connection for each of the input data source, the data analysis engine and the data output, wherein the computer system comprises at least one processor for executing as part of the data analysis engine of each module one or more support vector machines for generating a plurality of classes of data and at least one margin between classes;

(b) connect between a web server and the web server connection of each module for communicating with each of the input data source, the data analysis engine and the data output of the corresponding module and for providing means for monitoring one or more of the input data source, the data analysis engine, and the data output;

(c) combine the data output from the plurality of modules to generate a single output representing results obtained from analyzing the plurality of heterogeneous data types; and (d) generate a display of organized analysis results;

wherein the at least one processor executes multiple iterations of a feature subset ranking algorithm on a plurality of data sets comprising one or more of sub-samples of the same data set, multiple data sets of heterogeneous data types, and heterogeneous data sources, to produce ranked lists of feature subsets;

wherein the heterogeneous data types comprise one or more data types selected from the group consisting of gene expression data, mass spectrometry data, 2-D gel data, antibody screening, clinical observations, clinical history, physical and chemical measurements, genomic determinations, proteomic determinations, drug levels, hormonal and immunological tests, neurochemical or neurophysical measurements, mineral and vitamin level determinations, and genetic and familial histories, and wherein the heterogeneous data sources comprises one or more data sources selected from the group consisting of sensor instruments for collection of genomic data, sensor instruments for collection of proteomic data, sensor instruments for collection of physical and chemical measurements, clinical record databases, general internet search engines, on-line genetic databases, on-line proteomic databases, and on-line journals; and wherein the ranked lists of feature subsets comprise lists of genes or proteins.

13. The computer program product of claim 12, wherein the computer processor is further programmed to execute at least one pre-processing algorithm for pre-processing the input data for each module.

14. The computer program product of claim 12, wherein the feature subset ranking algorithm comprises recursive feature elimination.

15. The computer program product of claim 12, wherein the computer processor is further programmed to generate an observation tree for visually displaying the ranked list of genes or proteins.

16. The computer program product of claim 12, wherein the computer processor is further programmed to validate an analysis obtained with one data type with the analysis obtained with another data type.

17. The computer program product of claim 15, wherein the observation tree comprises a plurality of nodes, wherein each node of the tree is labeled with a gene or protein and a corresponding feature subset score.

18. The computer program product of claim 17 wherein the plurality of nodes comprises root nodes and child nodes, wherein the genes or proteins corresponding to the child nodes represent alternate choices for the genes or proteins corresponding to the root nodes.

19. The computer program product of claim 18 wherein the plurality of nodes further comprises grandchild nodes, wherein the genes or proteins corresponding to the grandchild nodes represent alternate choices for the genes or proteins corresponding to the root nodes and the child nodes.

20. The computer program product of claim 18, wherein the alternate choices for genes or proteins are selected based upon expert knowledge.

21. The computer program product of claim 18, wherein the alternate choices for genes or proteins are selected based upon information obtained from a different data source.

22. The computer program product of claim 18, wherein the alternate choices for genes or proteins are selected based upon ease of detection in a biological sample.

* * * * *